United States Patent
Reiffenrath et al.

(10) Patent No.: US 7,122,228 B2
(45) Date of Patent: Oct. 17, 2006

(54) COMPOUND HAVING NEGATIVE Δε

(75) Inventors: Volker Reiffenrath, Rossdorf (DE); Michael Heckmeier, Darmstadt (DE); Matthias Bremer, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/484,193

(22) PCT Filed: Jul. 19, 2002

(86) PCT No.: PCT/EP02/08085

§ 371 (c)(1),
(2), (4) Date: Jan. 20, 2004

(87) PCT Pub. No.: WO03/010120

PCT Pub. Date: Feb. 6, 2003

(65) Prior Publication Data

US 2004/0171866 A1    Sep. 2, 2004

(30) Foreign Application Priority Data

Jul. 20, 2001    (DE) ................. 101 35 499

(51) Int. Cl.
C09K 19/34 (2006.01)
C09K 19/32 (2006.01)
C07D 307/78 (2006.01)
C07C 25/22 (2006.01)
C07C 49/323 (2006.01)

(52) U.S. Cl. ............ 428/1.1; 252/299.61; 252/299.62; 252/299.63; 549/469; 549/470; 570/127; 570/129; 570/183; 568/330

(58) Field of Classification Search .......... 252/299.01, 252/299.61, 299.62, 299.63; 428/1.1; 549/469, 549/470; 568/330; 570/127, 129, 183
See application file for complete search history.

(56) References Cited

U.S. PATENT DOCUMENTS

| | | | |
|---|---|---|---|
| 2,447,099 A | | 8/1948 | Ulrich |
| 4,659,709 A | * | 4/1987 | Harada et al. ............ 514/232.5 |
| 6,878,421 B1 | * | 4/2005 | Heckmeier et al. ......... 428/1.1 |
| 2003/0222243 A1 | * | 12/2003 | Lietzau et al. ......... 252/299.61 |

FOREIGN PATENT DOCUMENTS

| | | |
|---|---|---|
| DE | 279 864 | 10/1913 |
| DE | 43 03 634 | 8/1994 |
| DE | 199 00 517 | 7/1999 |
| DE | 199 09 761 | 10/1999 |
| JP | 08 157463 | 6/1996 |
| JP | 08 169883 | 7/1996 |

OTHER PUBLICATIONS

Caplus 1987: 102473.*
M. Watanbe et al., "A Regioselective Lithiation of Ortho-Cresols Using the Bis(Dimethylamino)Phosphoryl Group as a Directing Group . . .", *Chemical and Pharmaceutical Bulletin, Pharmaceutical Society of Japan*, Bd. 39, Nr. 12 (Dec. 1991).
P. Bavin et al, "Compounds Affecting the Central Nervous System v. Substituted 3-Dialklaminoalkylindenes", *Journal of Medicinal Chemistry*, Bd. 12, Nr. 3 (May 1, 1969).
B. Gates et al., "Mechanistic Aspects and Synthetic Applications . . . Styrene Derivatives", *Journal of Organic Chemistry*, Bd. 57 (1992).
L. Greifenstein, et al., "Response of Acidity and Magnetic Resonance . . . 3-Arylindenes", *Journal of Organic Chemistry*, Bd. 25, Nr. 46 (1981).
D. Lednicer et al., "Mammalian Antifertility Agents. I. Derivatives of 2,3-diphenylindenes", *J. Med. Chem.*, Bd. 8, (1965).
T. Suzuki et al., "Superacid-Catalyzed . . . Oxonium-Carbenium Dications", *J. Am. Chem. Soc.*, Bd. 119, Nr. 29 (1997).
C. Hurd et al., "Directed Ring Closure . . . From O-Allylphenols", *J. Org. Chem.*, Bd. 5 (1940).
R. Larock et al., "Palladium-Catalyzed . . . Aryl Halides", *J. Org. Chem.*, Bd. 55, Nr. 11 (1990).
G. Jha et al., "Synthesis of Indeno'2,1-clisocoumarins & indeno'2,1-clisoquinolones", *Indian J. Chem.*, Bd. 24B, (1985).
P. Bickert et al., "Phane des 1,5- und 1,7-Dihydro-s-indacens", *Angew. Chem.*, Bd. 94, Nr. 4 (1982).
P. Ruggli et al., "Uber die Synthese eines Linearen Dioxo-dicyclopenteno-benzols", *Helv. Chim. Acta*, Bd. 30, (1947).

* cited by examiner

*Primary Examiner*—Shean C Wu
(74) *Attorney, Agent, or Firm*—Miller, White, Zelano, Branigan, P.C.

(57) ABSTRACT

The invention relates to indanes having negative Δε of the formula Ia or Ib

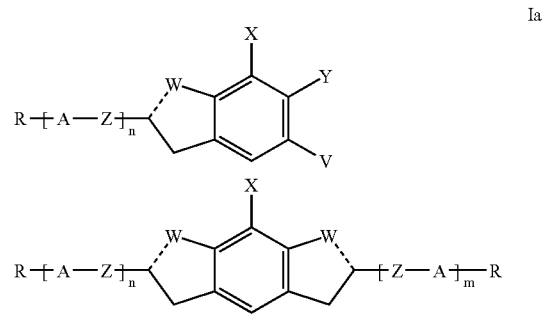

in which R, A, Z, X, Y, V, W, n and m are as defined in claim 1.

The compounds are particularly suitable for producing VA-TFT displays.

30 Claims, No Drawings

COMPOUND HAVING NEGATIVE Δε

The invention relates to indane compounds having negative Δε.

Liquid crystals have been widely used ever since the first commercially useful liquid-crystalline compounds were discovered 30 years ago. Typical application areas are in particular displays for watches and clocks or pocket calculators, or large display panels as used in stations, airports and sports arenas. Other application areas are displays of portable computers or navigation systems, and video applications. The latter applications in particular have to meet high requirements on switching times and image contrast.

As a result of the spatial order of the molecules in a liquid-crystal, many of its properties are anisotropic. Of particular importance for use in liquid-crystal displays are anisotropies in optical, dielectric and elasto-mechanic behavior. Depending on whether the longitudinal axes of the molecules are oriented parallel or perpendicular to the two plates of a capacitor, the latter has a different capacitance; therefore the dielectric constant ε of the liquid crystal differs in size for the two orientations. Substances whose dielectric constant is larger when the longitudinal axes of the molecules are oriented perpendicular to the capacitor plates are called dielectrically positive. Most liquid crystals used in conventional displays belong to this group.

The dielectric anisotropy is influenced both by the polarizability of the molecule and permanent dipole moments. On application of a voltage across the display, the longitudinal axis of the molecules is oriented such that the larger of the dielectric constants comes into effect. The strength of interaction with the electric field depends on the difference between the two constants. When the difference is small, higher switching voltages are required than when the difference is large. A wide range of operating voltages can be realized by introducing suitable polar groups such as nitrites (CN—) or fluorine into the liquid-crystal molecules.

In the liquid-crystalline molecules used in conventional liquid-crystal displays, the dipole moment along the longitudinal axis of the molecule is larger than the dipole moment perpendicular to the longitudinal axis of the molecule. The orientation of the larger dipole moment along the longitudinal axis of the molecule likewise determines the orientation of the molecule in a liquid-crystal display in the field-off state. In the most commonly used TN (twisted nematic) cells, a liquid-crystalline layer having a thickness of only 5 to 10 μm is interposed between two plane glass plates each of which has been coated by vapor deposition with an electrically conducting, transparent layer of tin oxide or indium-tin oxide as electrode. Between these films and the liquid-crystalline layer there is a likewise transparent alignment layer which is usually made of plastic (e.g. polyimides). Due to surface forces, this layer forces the longitudinal axes of adjacent crystalline molecules into a preferential direction such that, in the voltage-free case, they rest on the inside of the display surface uniformly and have the same orientation, either planar or having the same low tilt angle. Two polarizing films through which only linearly polarized light can pass are adhered to the outside of the display in specific arrangements.

Very efficient displays have been developed using liquid crystals in which the larger dipole moment is parallel to the longitudinal axis of the molecule. Mostly, mixtures of 5 to 20 components are used to achieve a sufficiently broad mesophase temperature range, short response times and low threshold voltages. However, difficulties are still caused by the high viewing angle dependence in liquid-crystal displays as used, for example, for laptops. Optimum image quality can be achieved when the display surface is perpendicular to the viewing direction of the observer. If the display is tilted relative to the viewing direction, image quality may deteriorate dramatically. To achieve a higher comfort, efforts are made to make the angle by which the display can be tilted away from the viewing angle of an observer as large as possible. Recently attempts have been made to improve the viewing angle dependence by using liquid-crystalline compounds whose dipole moment perpendicular to the longitudinal axis of the molecule is larger than that parallel to the longitudinal axis of the molecule. In the field-off state, these molecules are thus aligned perpendicular to the treated or coated glass surface of the display. This lead to an improvement in the viewing angle dependence. Such displays are called VA (vertical align) TFT displays.

There is still considerable scope for development in the field of liquid-crystalline materials. Continuous attempts are being made to improve the properties of liquid-crystalline display elements by developing novel compounds which make it possible to optimize such displays.

It is therefore an object of the invention to provide liquid-crystalline compounds having advantageous properties.

This object is achieved by compounds of the formula (Ia) or (Ib)

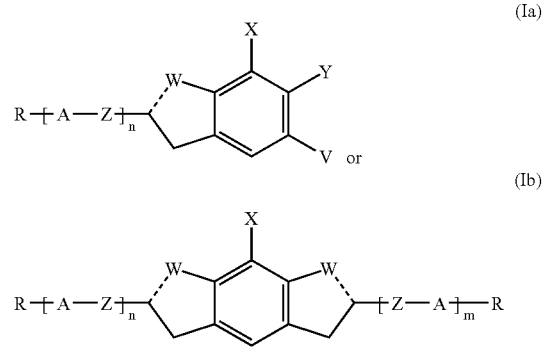

in which:

R, in each case independently of one another, is an alkyl or alkoxy radical having 1 to 12 carbon atoms which is unsubstituted, monosubstituted by —CF$_3$ or at least monosubstituted by halogen, an oxaalkyl, alkenyl or alkenyloxy radical having 2 to 12 carbon atoms or an oxaalkenyl radical having 3 to 12 carbon atoms, where one or more CH$_2$ groups in these radicals may also, in each case independently of one another, be replaced by —O—, —S—, —CO—, —COO—, —OCO— or —OCO—O— in such a way that heteroatoms are not linked directly to one another, A, in each case independently of one another, is 1,4-phenylene, in which =CH— may be replaced once or twice by =N— and which may be mono- to tetrasubstituted, independently of one another, by halogen (—F, —Cl, —Br, —I), —CN, —CH$_3$, —CH$_2$F, —CHF$_2$, —CF$_3$, —OCH$_3$, —OCH$_2$F, —OCHF$_2$ or —OCF$_3$, 1,4-cyclohexylene, 1,4-cyclohexenylene or 1,4-cyclohexadienylene, in which —CH$_2$— may be replaced once or twice by, independently of one another, —O— or —S— and which may be mono- or polysubstituted by halogen, Z, in each case independently of one another, is a single bond, a —CH$_2$—CH$_2$—, —CF$_2$CF$_2$—, —CH═CH—, —CF═CH—, —CH═CF—, —C≡C—, —CO—O—, —O—CO—, —O—CH$_2$—, —CH$_2$—O—, O—CF$_2$— or a —CF$_2$—O— group, X is —H, —F, —Cl, —CN, —NCS, —CF$_3$, —OCF$_3$, —OCHF$_2$, Y, V are each, independently of one another, hydrogen, an alkyl, alkoxy, alkenyl or alkinyl radical having 1 to 15 or, respectively, 2 bis 15 carbon atoms which is unsubstituted, mono-substituted by —CF$_3$ or at least mono-substituted by halogen where one or more CH$_2$ groups in these radicals may also, in each case independently of one another, be replaced by —O—, —S—, —CO—, —COO—, —OCO— or —OCO—O— in such a way that heteroatoms are not linked directly to one another, Y is additionally —F or —Cl, W, in each case independently of one another, is —O—, —C(O)—, —CHF— or —CF$_2$— or —CH═ or —CF═ and, in formula (Ib), additionally —CH$_2$— n, m are each, independently of one another, 0, 1, 2, 3 or 4 and the dotted line is a single bond or a double bond, with the proviso that X in formula (Ib)≠H when W is twice —CH$_2$—. In the general formulae (Ia) and (Ib), A is in each case independently of one another preferably unsubstituted or substituted 1,4-phenylene, unsubstituted or substituted 1,4-cyclohexylene, in which —CH$_2$— may be replaced once or twice by —O—, or unsubstituted or substituted 1,4-cyclohexenylene.

Particularly preferably, A is in each case independently of one another

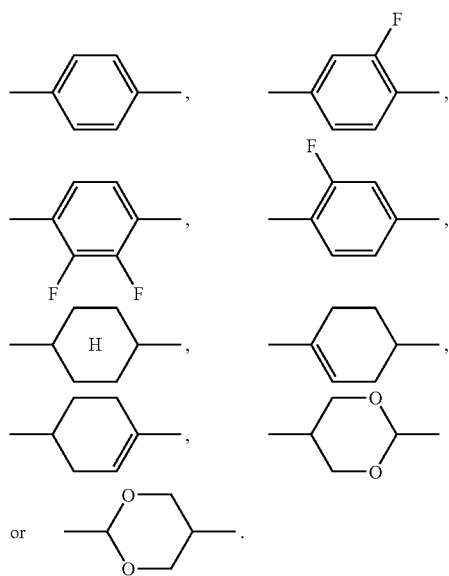

R, Y and V in the general formulae (Ia) and (Ib) may each, independently of one another, be an alkyl radical and/or an alkoxy radical having 1 to 15 carbon atoms which can be straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, methoxy, ethoxy, propoxy, butoxy, pentoxy hexoxy or heptoxy.

R, Y and V can each, independently of one another, be oxaalkyl, preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl.

R, Y and W can each, independently of one another, be an alkenyl radical having 2–15 carbon atoms which can be straight-chain or branched. It is preferably straight-chain and has 2 to 7 carbon atoms. Accordingly, it is in particular vinyl, prop-1- or prop-2-enyl, but-1-, -2- or but-3-enyl, pent-1-, -2-, -3- or pent4-enyl, hex-1-, -2-, -3-, 4- or hex-5-enyl, hept-1-, -2-, -3-4-, -5- or hept-6-enyl.

R, Y and V can each, independently of one another, be an alkyl radical having 1 to 15 carbon atoms in which one CH$_2$ group has been replaced by —O— and one has been replaced by —CO—, these being preferably adjacent. These thus contain an acyloxy group —CO—O— or an oxycarbonyl group —O—CO—. These are preferably straight-chain and have 2 to 6 carbon atoms.

R, Y and V can each, independently of one another, be an alkyl radical having 1 to 15 carbon atoms in which one CH$_2$ group has been replaced by unsubstituted or substituted —CH═CH— and an adjacent CH$_2$ group has been replaced by —CO— or —CO—O— or —O—CO—, in which case this can be straight-chain or branched. It is preferably straight-chain and has 4 to 13 carbon atoms.

R, Y and V can each, independently of one another, be an alkyl radical having 1 to 15 carbon atoms or an alkenyl radical having 2 to 15 carbon atoms which is monosubstituted by —CN or —CF$_3$, these radicals being preferably straight-chain. The substitution by —CN or —CF$_3$ is in any position.

R, Y and V can each, independently of one another, be an alkyl radical having 1 to 15 carbon atoms or an alkenyl radical having 2 to 15 carbon atoms which is at least monosubstituted by halogen, this radical being preferably straight-chain and halogen is preferably —F or —Cl. In the case of polysubstitution, halogen being preferably —F. The resulting radicals also include perfluorinated radicals. In the case of monosubstitution, the fluoro or chloro substituent can be in any desired position, but is preferably in the ω-position.

R, Y and V can each, independently of one another, be an alkyl radical in which two or more CH$_2$ groups are replaced by —O— and/or —CO—O—, in which case this radical can be straight chain or branched. It is preferably branched and has 3 to 12 carbon atoms.

R, Y and V in the general formulae (Ia) and (Ib) are preferably hydrogen or an alkyl radical, alkoxy radical or alkenyl radical having 1 to 7 or, respectively, 2 to 7 carbon atoms.

Y is additionally preferably —F or —Cl, in particular —F.

Preferred indanes of the general formula (Ia) or (Ib) contain one or two A cycles.

The compounds have a negative Δε and are therefore suitable for use in VA TFT displays. They exhibit a very good compatibility with the usual substances used in liquid-crystal mixtures for displays.

The substituents X and W in the indane skeleton generates a dipole moment perpendicular to the longitudinal axis of the molecule which may be increased, if desired, by suitable substituents in the pendant moieties ZAZAR. In the field-off state, the compounds of the formulae (Ia) or (Ib) orientate such that their longitudinal axis of the molecule is perpendicular to the glass surface of a display.

The following groups of compounds, in which W, V, A, Y, Z, R, n and m are as defined above, were found to be particularly suitable.

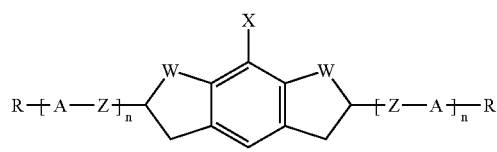
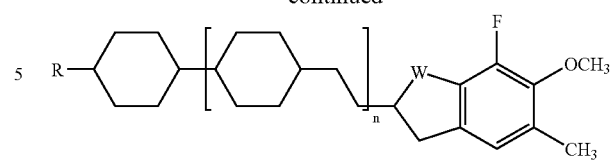
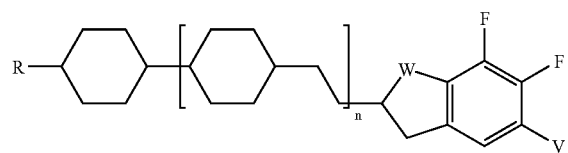
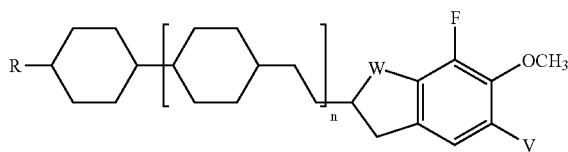
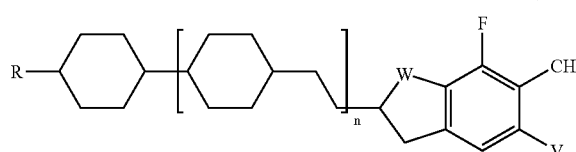
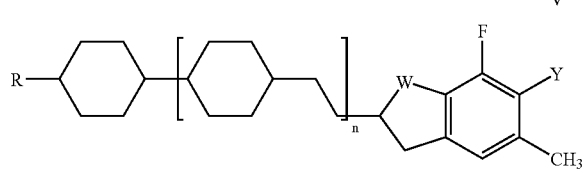
The following compounds are especially suitable:
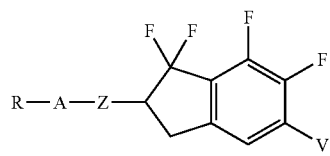
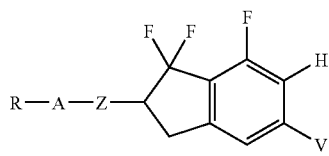
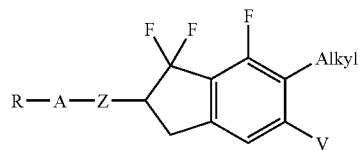
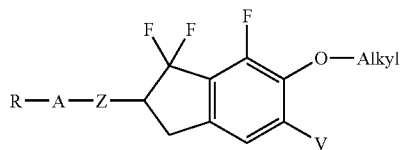
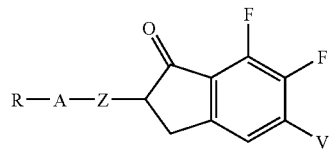
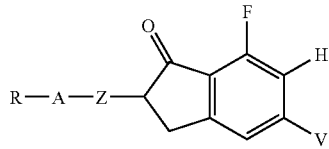
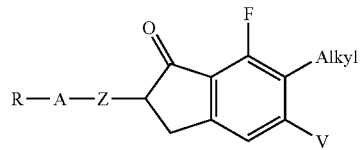
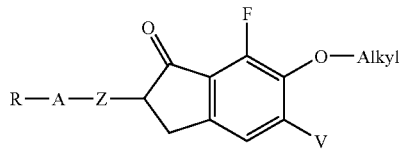

-continued
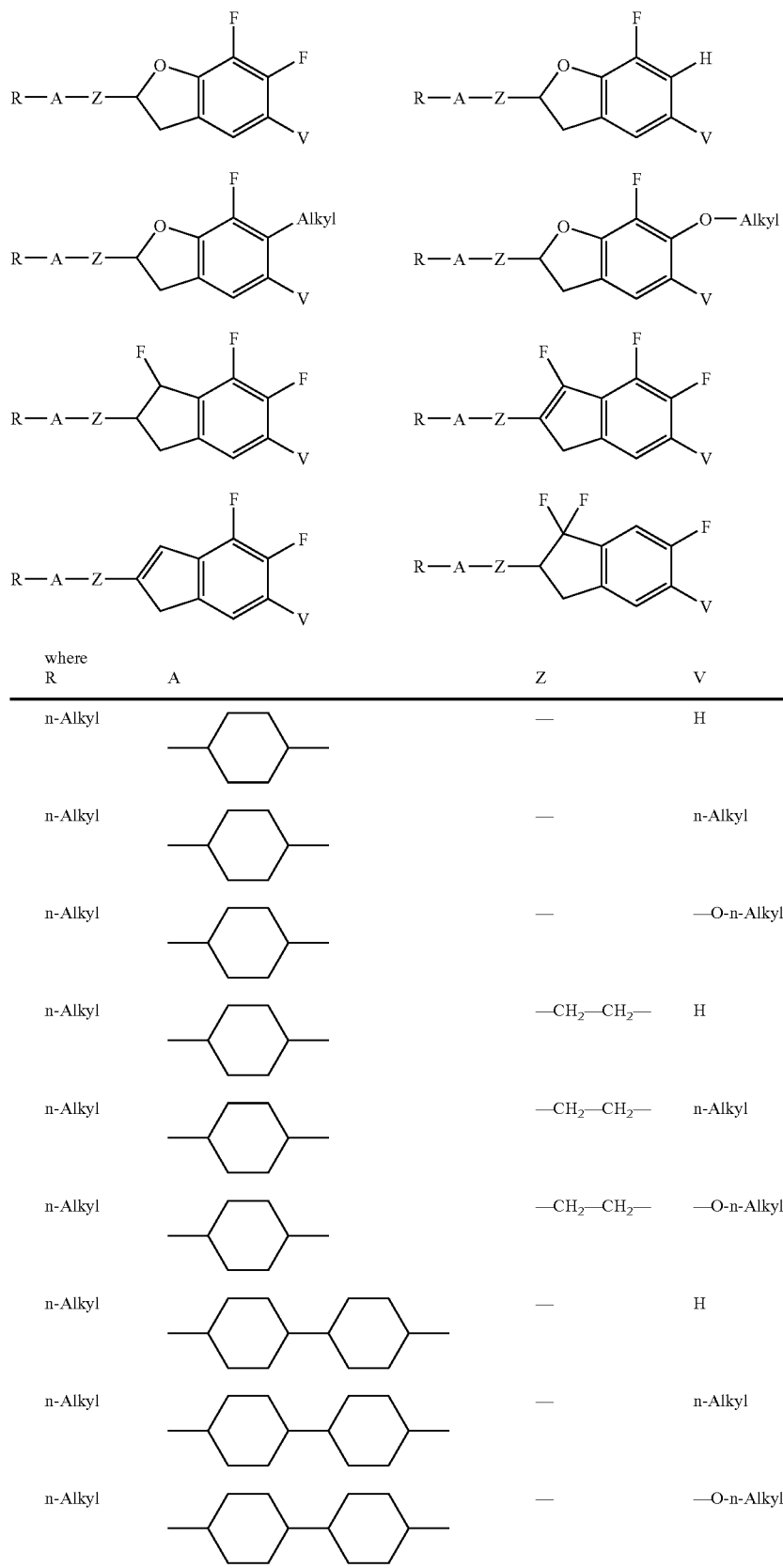

-continued

| R¹ | Ring | Linker | R² |
|---|---|---|---|
| n-Alkyl | Cyclohexyl-Cyclohexyl | —CH₂—CH₂— | H |
| n-Alkyl | Cyclohexyl-Cyclohexyl | —CH₂—CH₂— | n-Alkyl |
| n-Alkyl | Cyclohexyl-Cyclohexyl | —CH₂—CH₂— | —O-n-Alkyl |
| n-Alkyl | Phenyl | — | H |
| n-Alkyl | Phenyl | — | n-Alkyl |
| n-Alkyl | Phenyl | — | —O-n-Alkyl |
| n-Alkyl | Phenyl | —CH₂—CH₂— | H |
| n-Alkyl | Phenyl | —CH₂—CH₂— | n-Alkyl |
| n-Alkyl | Phenyl | —CH₂—CH₂— | —O-n-Alkyl |
| n-Alkyl | Cyclohexyl-Phenyl | — | H |
| n-Alkyl | Cyclohexyl-Phenyl | — | n-Alkyl |
| n-Alkyl | Cyclohexyl-Phenyl | — | —O-n-Alkyl |
| n-Alkyl | Cyclohexyl-Phenyl | —CH₂—CH₂— | H |
| n-Alkyl | Cyclohexyl-Phenyl | —CH₂—CH₂— | n-Alkyl |
| n-Alkyl | Cyclohexyl-Phenyl | —CH₂—CH₂— | —O-n-Alkyl |
| n-Alkyl | Phenyl-Phenyl | — | H |

-continued

| | | | |
|---|---|---|---|
| n-Alkyl | biphenyl | — | n-Alkyl |
| n-Alkyl | biphenyl | — | —O-n-Alkyl |
| n-Alkyl | biphenyl | —CH$_2$—CH$_2$— | H |
| n-Alkyl | biphenyl | —CH$_2$—CH$_2$— | n-Alkyl |
| n-Alkyl | biphenyl | —CH$_2$—CH$_2$— | —O-n-Alkyl |
| n-Alkyl | cyclohexyl | —CH$_2$—O— | H |
| n-Alkyl | cyclohexyl | —CH$_2$—O— | n-Alkyl |
| n-Alkyl | cyclohexyl | —CH$_2$—O— | —O-n-Alkyl |
| n-Alkyl | cyclohexyl | —O—CH$_2$— | H |
| n-Alkyl | cyclohexyl | —O—CH$_2$— | n-Alkyl |
| n-Alkyl | cyclohexyl | —O—CH$_2$— | —O-n-Alkyl |
| n-Alkyl | bicyclohexyl | —CH$_2$—O— | H |
| n-Alkyl | bicyclohexyl | —CH$_2$—O— | n-Alkyl |
| n-Alkyl | bicyclohexyl | —CH$_2$—O— | —O-n-Alkyl |
| n-Alkyl | bicyclohexyl | —O—CH$_2$— | H |
| n-Alkyl | bicyclohexyl | —O—CH$_2$— | n-Alkyl |

-continued

| R¹ | ring | linker | R² |
|---|---|---|---|
| n-Alkyl | cyclohexyl-cyclohexyl | —O—CH₂— | —O-n-Alkyl |
| n-Alkyl | phenyl | —O—CH₂— | H |
| n-Alkyl | phenyl | —O—CH₂— | n-Alkyl |
| n-Alkyl | phenyl | —O—CH₂— | —O-n-Alkyl |
| n-Alkyl | cyclohexyl-CH₂CH₂-cyclohexyl | — | H |
| n-Alkyl | cyclohexyl-CH₂CH₂-cyclohexyl | — | n-Alkyl |
| n-Alkyl | cyclohexyl-CH₂CH₂-cyclohexyl | — | —O-n-Alkyl |
| n-Alkyl | cyclohexyl-CH₂CH₂-cyclohexyl | —CH₂—CH₂— | H |
| n-Alkyl | cyclohexyl-CH₂CH₂-cyclohexyl | —CH₂—CH₂— | n-Alkyl |
| n-Alkyl | cyclohexyl-CH₂CH₂-cyclohexyl | —CH₂—CH₂— | —O-n-Alkyl |
| n-Alkyl | cyclohexyl-CH₂CH₂-phenyl | — | H |
| n-Alkyl | cyclohexyl-CH₂CH₂-phenyl | — | n-Alkyl |
| n-Alkyl | cyclohexyl-CH₂CH₂-phenyl | — | —O-n-Alkyl |

-continued
| | | | |
|---|---|---|---|
| n-Alkyl | 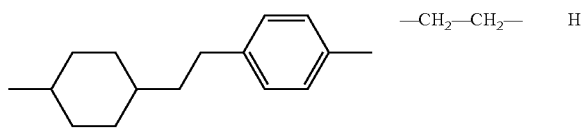 | —CH$_2$—CH$_2$— | H |
| n-Alkyl | 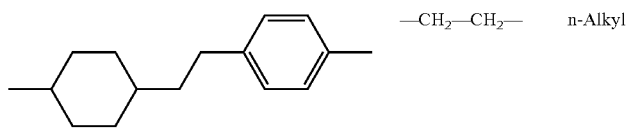 | —CH$_2$—CH$_2$— | n-Alkyl |
| n-Alkyl | 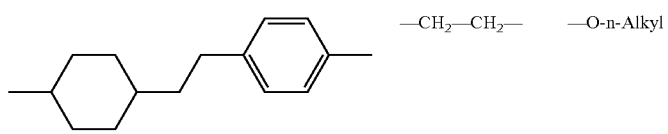 | —CH$_2$—CH$_2$— | —O-n-Alkyl |
| n-Alkyl-O— |  | — | H |
| n-Alkyl-O— |  | — | n-Alkyl |
| n-Alkyl-O— |  | — | —O-n-Alkyl |
| n-Alkyl |  | — | H |
| n-Alkyl |  | — | n-Alkyl |
| n-Alkyl |  | — | —O-n-Alkyl |
| n-Alkyl | 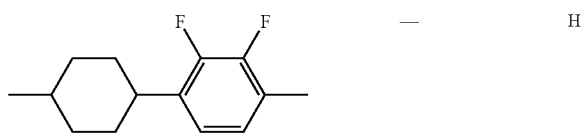 | — | H |
| n-Alkyl | 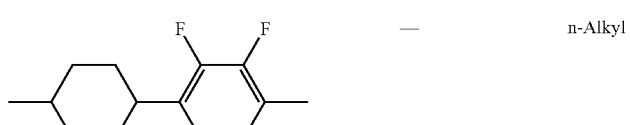 | — | n-Alkyl |
| n-Alkyl |  | — | —O-n-Alkyl |

-continued
| | | | |
|---|---|---|---|
| n-Alkyl | 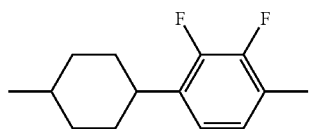 | —CH₂—CH₂— | H |
| n-Alkyl | 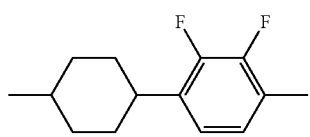 | —CH₂—CH₂— | n-Alkyl |
| n-Alkyl | 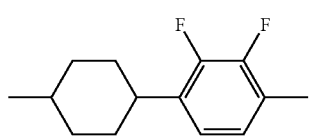 | —CH₂—CH₂— | —O-n-Alkyl |
| n-Alkyl | 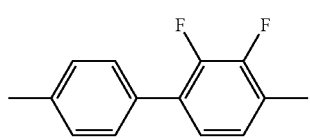 | — | H |
| n-Alkyl | 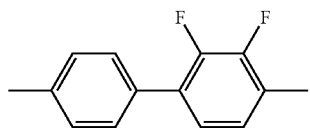 | — | n-Alkyl |
| n-Alkyl | 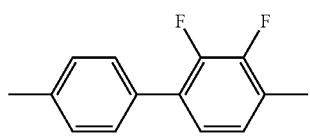 | — | —O-n-Alkyl |
| n-Alkyl-O— | 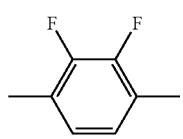 | — | H |
| n-Alkyl-O— | 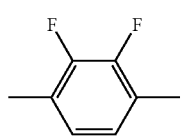 | — | n-Alkyl |
| n-Alkyl-O— | 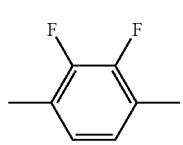 | — | —O-n-Alkyl |

-continued

| where R | A | Z |
|---|---|---|
| n-Alkyl | cyclohexyl | — |
| n-Alkyl | cyclohexyl | —CH₂—CH₂— |
| n-Alkyl | dicyclohexyl | — |
| n-Alkyl | dicyclohexyl | —CH₂—CH₂— |
| n-Alkyl | phenyl | — |
| n-Alkyl | phenyl | —CH₂—CH₂— |
| n-Alkyl | cyclohexyl-phenyl | — |
| n-Alkyl | cyclohexyl-phenyl | —CH₂—CH₂— |
| n-Alkyl | biphenyl | — |
| n-Alkyl | biphenyl | —CH₂—CH₂— |
| n-Alkyl | cyclohexyl | —CH₂—O— |
| n-Alkyl | cyclohexyl | —O—CH₂— |

-continued
| | | |
|---|---|---|
| n-Alkyl | 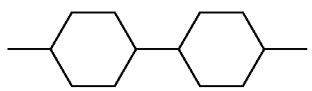 | —CH$_2$—O— |
| n-Alkyl | 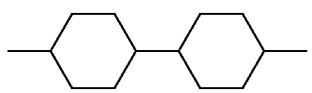 | —O—CH$_2$— |
| n-Alkyl | 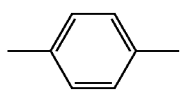 | —O—CH$_2$— |
| n-Alkyl | 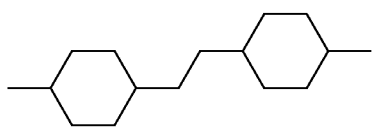 | — |
| n-Alkyl | 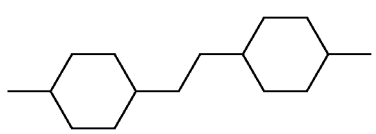 | —CH$_2$—CH$_2$— |
| n-Alkyl | 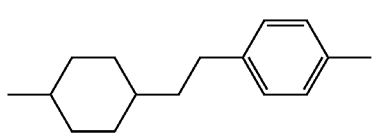 | — |
| n-Alkyl | 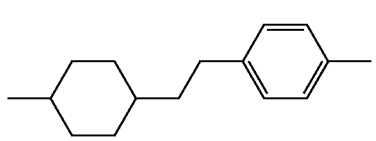 | —CH$_2$—CH$_2$— |
| n-Alkyl-O | 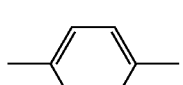 | — |
| n-Alkyl | 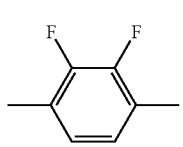 | — |
| n-Alkyl | 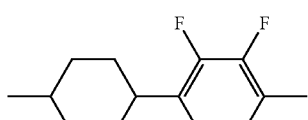 | — |
| n-Alkyl | 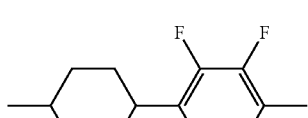 | —CH$_2$—CH$_2$— |
| n-Alkyl | 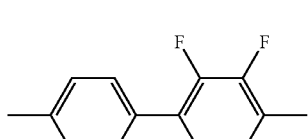 | — |

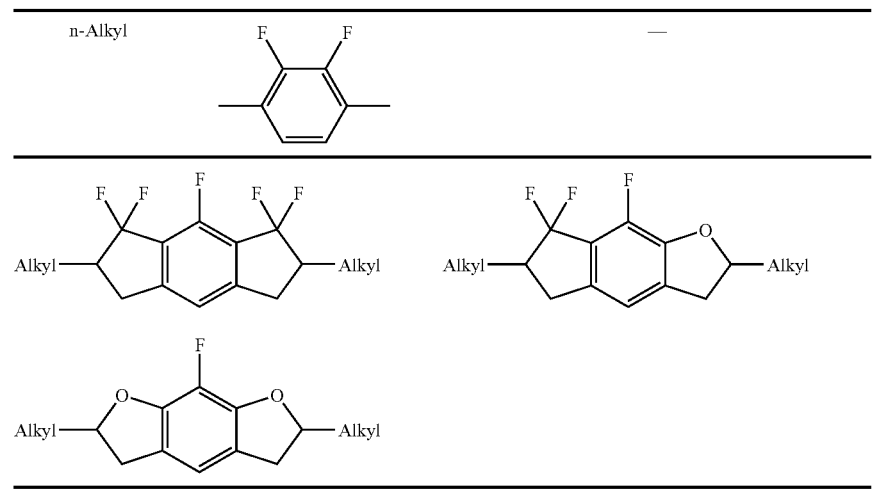
The following structures are very particularly preferred:
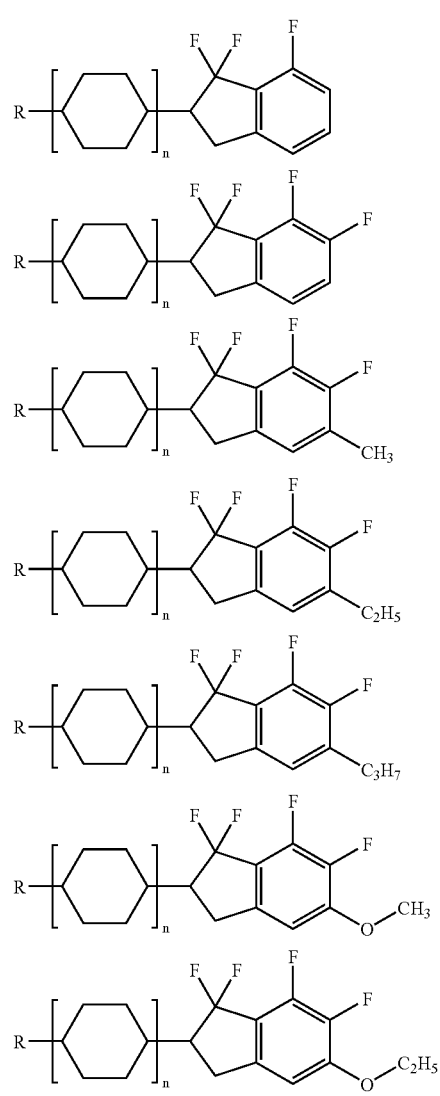
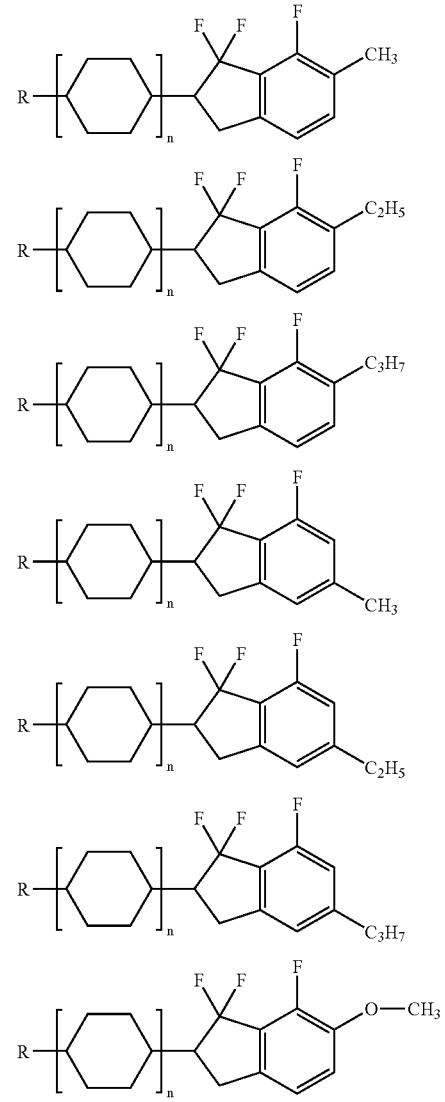

-continued

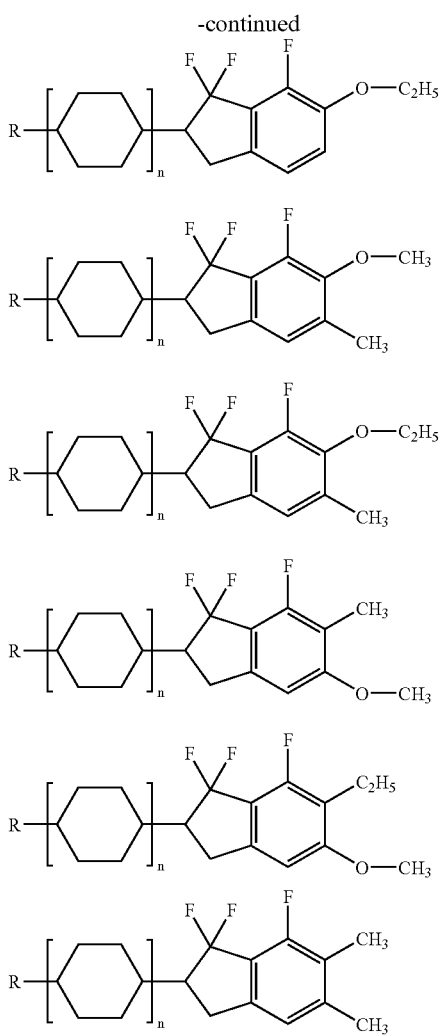

From the last-mentioned-very-particularly preferred structures, those are especially preferred in which n=1 and R=n-alkyl, in particular $C_1-C_5$-alkyl, n=2 and R=n-alkyl, in particular $C_1-C_5$-alkyl, n=1 and R=n-alkenyl, in particular vinyl, prop-1-enyl, but-1-enyl and but-3-enyl, n=2 and R=n-alkenyl, in particular vinyl, prop-1-enyl, but-1-enyl and but-3-enyl.

The compounds of the formula (Ia) and (Ib) are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions. Use can also be made here of variants which are known per se, but are not mentioned here in greater detail.

If desired, the starting materials can also be formed in situ such that they are not isolated from the reaction mixture but immediately reacted further to give compounds of the formula (Ia) or (Ib).

An exemplary synthesis is shown below. By choosing appropriate starting materials, the synthesis can be adapted to provide the compounds of the formula (Ia) or (Ib) desired in each case.

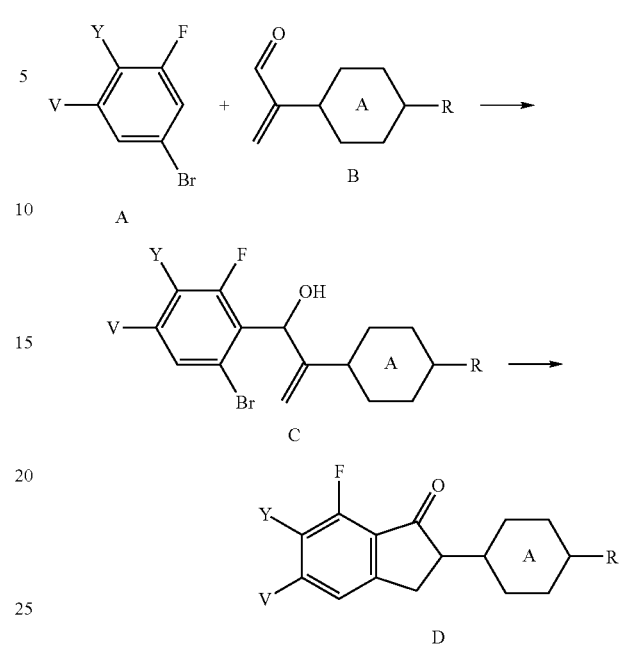

3-Bromofluorobenzene A, is reacted with the α, β-unsaturated aldehyde B in the presence of lithium diisopropylamide to give the compound C. In the presence of a palladium catalyst and of triethylamine, this compound undergoes a ring closure reaction to give the indanone D.

FIG. 2

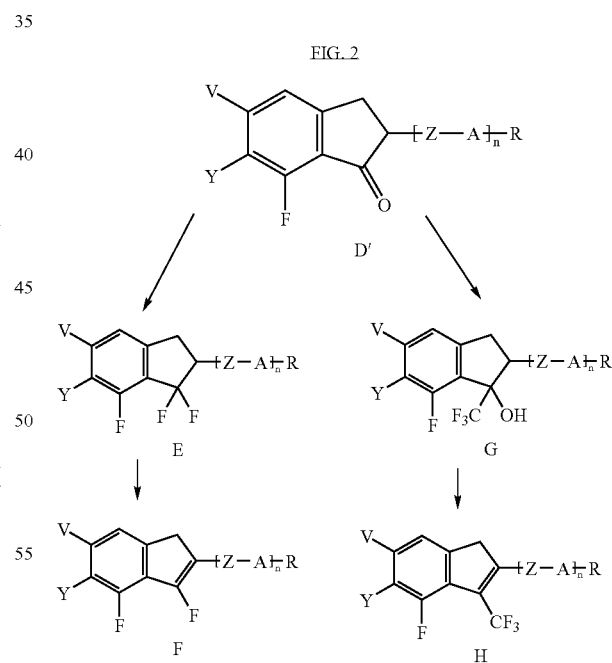

Fluorination of the keto compound D' using a suitable fluorinating agent, such as DAST or $SF_4$, gives the difluoro compound E, from which hydrogen fluoride can be eliminated, if necessary using a strong base such as potassium tert-butylate, resulting in compound F. A trifluoromethyl group can be introduced into the molecule by reaction with F$_3$CSi(CH$_3$)$_3$ followed by treatment with KF/CH$_3$OH (G). Subsequent dehydration using SOCl$_2$/Pyridine gives compound H.

Alternatively, the indanone D' can be reacted further as shown in FIG. 2a.

FIG. 2a

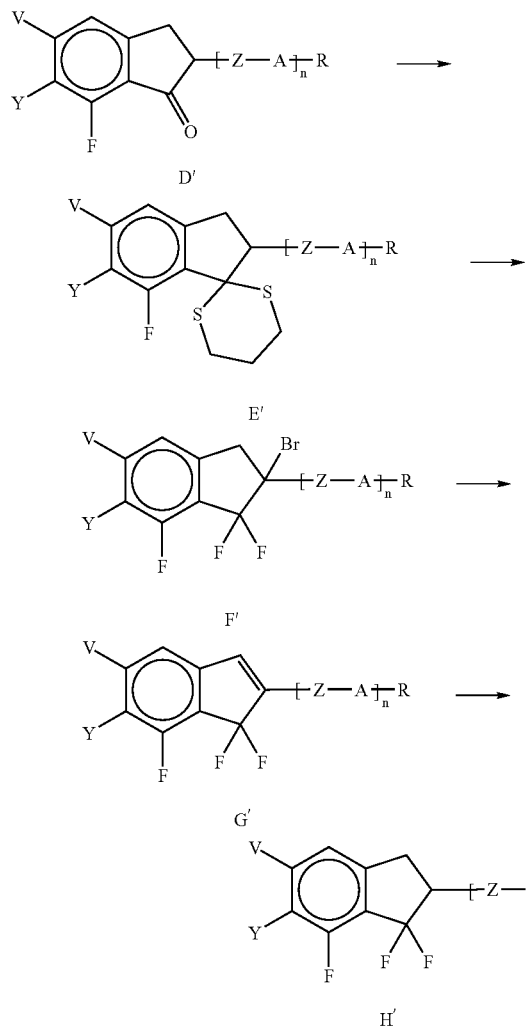

The keto compound D' is reacted with propane-1,3-dithiol to give the cyclic thioketal E'. Reaction with HF-pyridine in the presence of dibromodimethylhydantoin already gives the end product H' but also a certain amount of the bromide F'. The mixture is treated with base to eliminate HBr from compound F' which gives compound G'. Compound G' is then hydrogenated in the mixture of G' and H' to give the end product H'.

Further possibilites for forming the indane skeleton are shown in FIG. 3.

FIG. 3

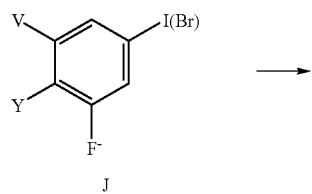

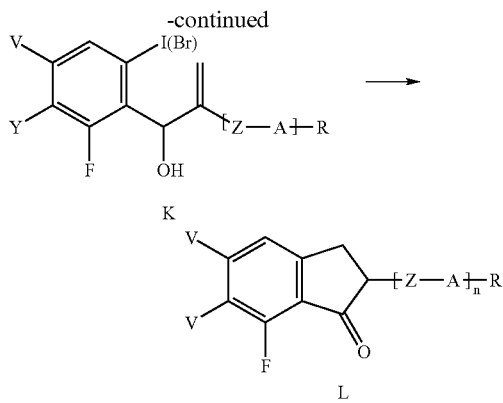

A suitably substituted iodobenzene derivative J is first deprotonated at a low temperature using a strong base, such as LDA, and then reacted wth a suitable acrolein derivative to give the alcohol K. Ring closure to give compound L is carried out by Heck reaction.

Benzofurans and dihydrobenzofurans according to the invention can be prepared in accordance with the general reaction sequence shown in FIG. 4.

FIG. 4

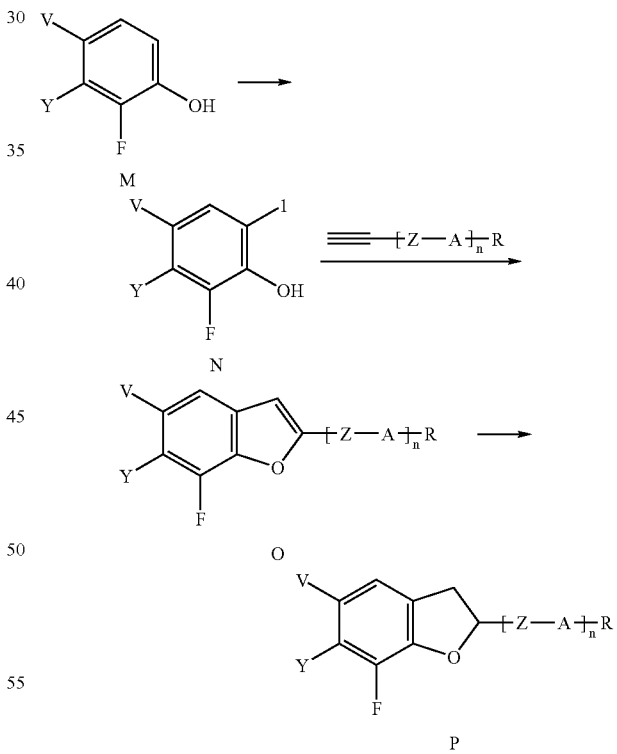

The starting phenol derivative M is first reacted with iodine in the presence of a weak base to introduce an iodo group which gives compound N. Subsequent ring closure by reacting with a suitable acetylene derivative in the presence of a palladium(II) compound, such as palladium(II) acetate, as catalyst produces the benzofuran derivative O. The latter can be hydrogenated catalytically over palladium/carbon to give the dihydrobenzofuran derivative P.

Indacenes according to the invention can be obtained in accordance with the reaction sequence shown in FIG. 5.

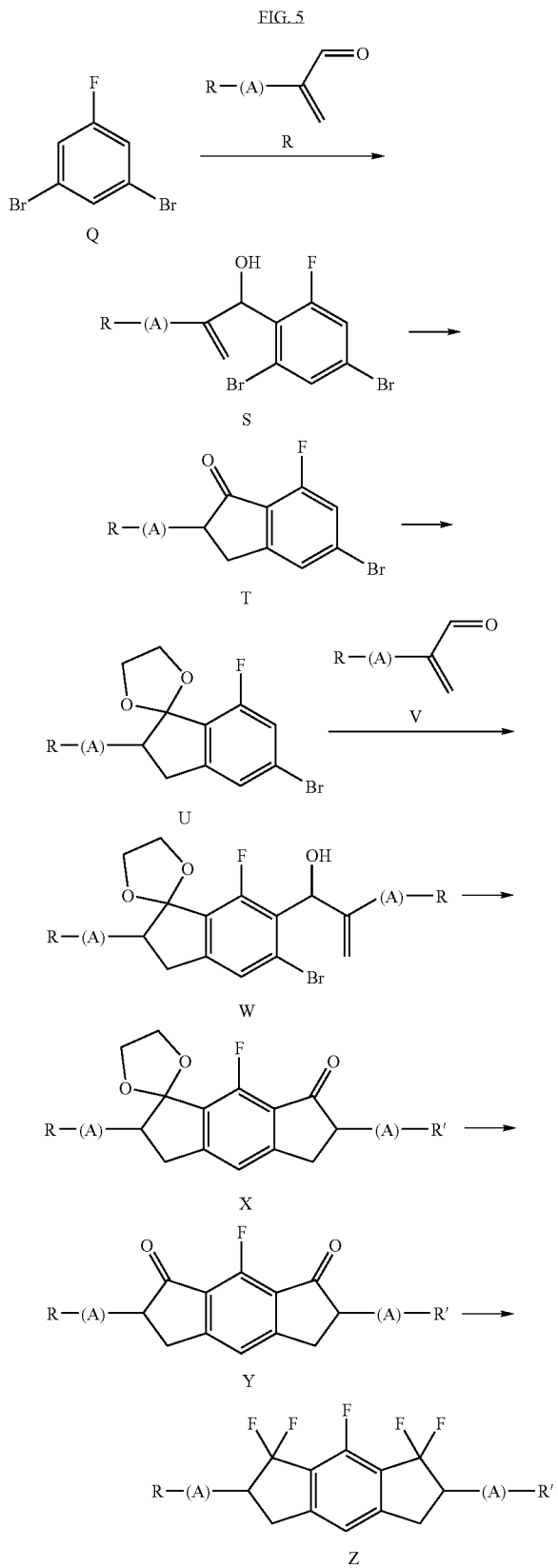

FIG. 5

The starting 3,5-dibromofluorobenzene Q is reacted with the unsaturated aldehyde R in the presence of lithium diisopropylamide to obtain compound S. The latter undergoes ring closure to give the indanone T in the presence of a palladium catalyst and triethylamine. Following ketalization of the keto group using ethylene glycol in the presence of toluenesulfonic acid, this process is repeated using the unsaturated aldehyde V to give the indacene X. Removal of the protective group by means of an acid gives the diketone Y which can be converted into the end product Z by means of suitable fluorinating agents such as $SF_4$.

The reactions shown are to be construed as merely illustrative. The person skilled in the art can modify the above discussed syntheses appropriately and use other suitable synthetic routes so as to obtain compounds of the formulae (Ia) and (Ib).

As mentioned above, the compounds of the formulae (Ia) and (Ib) can be used for producing liquid-crystalline mixtures. The invention therefore like-wise provides a liquid-crystalline medium comprising at least two liquid-crystalline compounds including at least one compound of the formulae (Ia) and (Ib).

The invention likewise provides liquid-crystalline media comprising 2 to 40, in particular 4 to 30, components as further constituents besides one or more compounds of the formulae (Ia) and/or (Ib) according to the invention. These media very particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4',4'-bis-cyclohexylbiphenyls, phenyl- or cyclohexylpyrimidines, phenyl- or cyclohexylpyridines; phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, halogenated or non-halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae (II), (III), (IV), (V) and (VI):

| | |
|---|---|
| R'-L-E-R" | (II) |
| R'-L-COO-E-R" | (III) |
| R'-L-OOC-E-R" | (IV) |
| R'-L-CH$_2$CH$_2$-E-R" | (V) |
| R'-L-CF$_2$O-E-R" | (VI) |

In the formulae (II), (III), (IV), (V) and (VI), L and E, which may be identical or different, are in each case, independently of one another, a bivalent radical from the group formed by -Phe-, -Cyc-, -Phe-Phe-, -Phe-Cyc-, -Cyc- Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc or Phe. E is preferably Cyc, Phe or Phe-Cyc. The media according to the invention preferably contain one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller subgroup of the compounds of the formulae (II), (III), (IV), (V) and (VI), R' and R" are in each case, independently of one another, alkyl, alkenyl, alkoxy, alkoxyalkyl, alkenyloxy or alkanoyloxy having up to 8 carbon atoms. This smaller subgroup is referred to as group A below, and the compounds are labelled with the subformulae (IIa), (IIIa), (IVa), (Va) and (VIa). In most of these compounds, R' and R" are different from one another, one of these radicals usually being alkyl, alkenyl, alkoxy or alkoxyalkyl.

In another smaller subgroup of the compounds of the formulae (II), (III), (IV), (V) and (VI) which is referred to as group B, E is

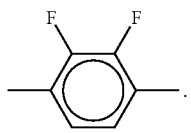

In the compounds of group B referred to using the subformulae (IIb), (IIIb), (IVb), (Vb) and (VIb), R' and R" are as defined for the compounds of the subformulae (IIa) to (VIa) and are preferably alkyl, alkenyl, alkoxy or alkoxyalkyl.

In a further smaller subgroup of the compounds of the formulae (II), (III), (IV), (V) and (VI), R" is -CN; this subgroup is referred to as group C below, and the compounds of this subgroup are correspondingly described by subformulae (IIc), (IIIc), (IVc), (Vc) and (VIc). In the compounds of the subformulae (IIc), (IIIc), (IVc), (Vc) and (VIc), R' is as defined for the compounds of the subformulae (IIa), (IIIa), (IVa), (Va) and (VIa) and is preferably alkyl, alkoxy or alkenyl.

In addition to the preferred compounds of groups A, B and C, other compounds of the formulae (II), (III), (IV), (V) and (VI) having other variants of the proposed substituents are also customary. All these substances can be obtained by methods which are known from the literature or analogously thereto.

Besides compounds of the formulae (Ia) and/or (Ib) according to the invention, the media according to the invention preferably contain one or more compounds selected from group A and/or group B and/or group C. The proportions by weight of the compounds from these groups in the media according to the invention are preferably

| | |
|---|---|
| Group A: | 0 to 90%, preferably 20 to 90%, in particular 30 to 90% |
| Group B: | 0 to 80%, preferably 10 to 80%, in particular 10 to 70% |
| Group C: | 0 to 80%, preferably 5 to 80%, in particular 5 to 50%, | the sum of the proportions by weight of the group A and/or B and/or C compounds present in the particular media according to the invention preferably being 5% to 90% and in particular 10% to 90%.

The media according to the invention preferably comprise 1 to 40%, particularly preferably 5 to 30%, of compounds of the formulae (Ia) and/or (Ib) according to the invention. Further preferred media are those which comprise more than 40%, in particular 45 to 90%, of compounds of the formulae (Ia) and/or (Ib) according to the invention. The media preferably comprise three, four or five compounds of the formulae (Ia) and/or (Ib) according to the invention.

Examples of the compounds of the formulae (II), (III), (IV), (V) and (VI) are the following compounds:

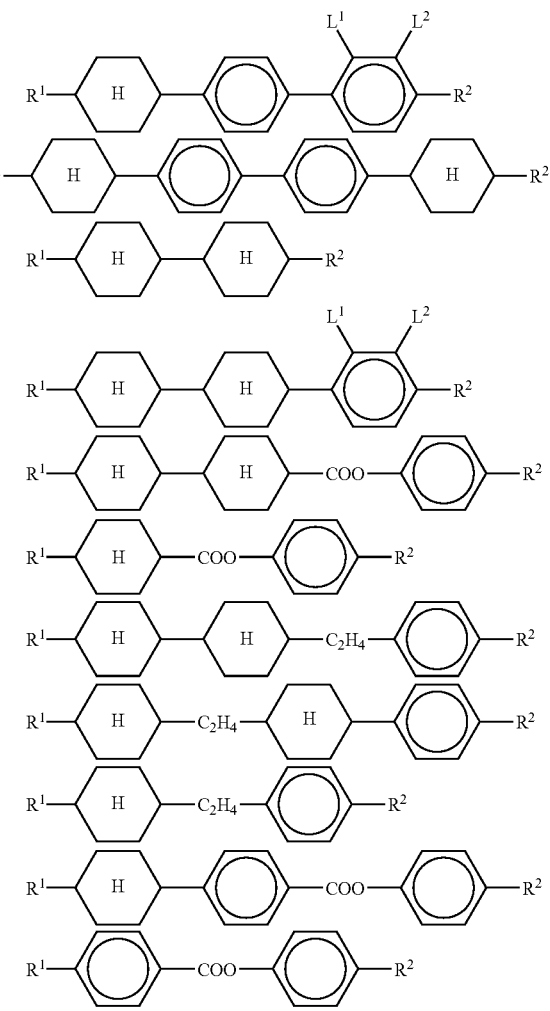

-continued
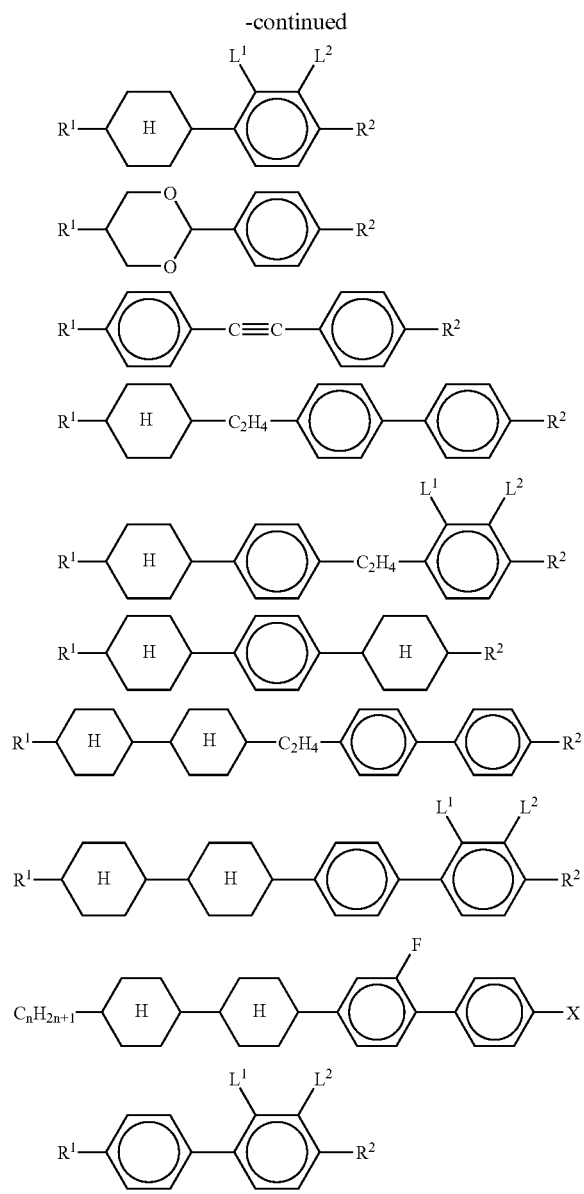
where $R^1$, $R^2$ =—$C_nH_{2n+1}$ where n=1–8 and $L^1$, $L^2$=—H or —F,
-continued
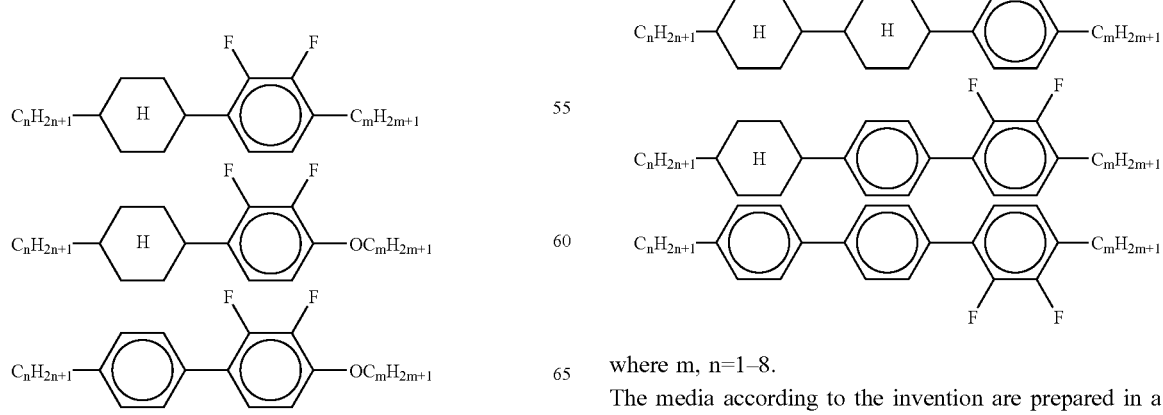
where m, n=1–8.
The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

Because of their negative $\Delta\epsilon$, the compounds of the formula (I) are suitable for use in VA TFT displays. The invention therefore likewise provides an electro-optical liquid-crystal display containing a liquid-crystalline medium according to the invention.

The examples below illustrate the invention:

EXAMPLES

SYNTHETIC EXAMPLES

Example 1

1-(2-Fluoro-6-iodo-4-methyl-phenyl)-2-(4'-propylbicyclohexyl-4-yl)-prop-2-en-1-ol

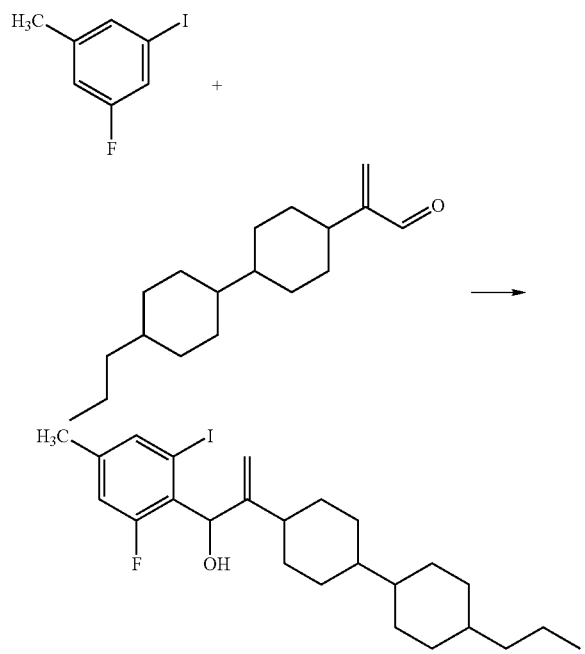

An initial charge of 31.1 g (0.22 mol) of 2,2,6,6-tetramethylpiperidine in 350 ml of tetrahydrofuran is cooled down to −20° C. 135 ml of 1.6 M butyllithium in hexane (0.22 mol) are added dropwise at this temperature. The mixture is cooled down to −18° C. and 47.2 g (0.2 mol) of 1-fluoro-3-iodo-5-methylbenzene are added dropwise at this temperature. The reaction mixture is stirred for another hour at −80° C. and then treated with 52.5 g (0.2 mol) of 3-(4'-propylbicyclohexyl-4-yl)propenal. The mixture is allowed to warm to 0° C., hydrolyzed with water and diluted hydrochloric acid and then subjected to conventional work-up.

Yield 75 g (75% of theory)

Example 2

7-Fluoro-5-methyl-2-(4'-propylbicyclohexyl-4-yl)-indan-1-one

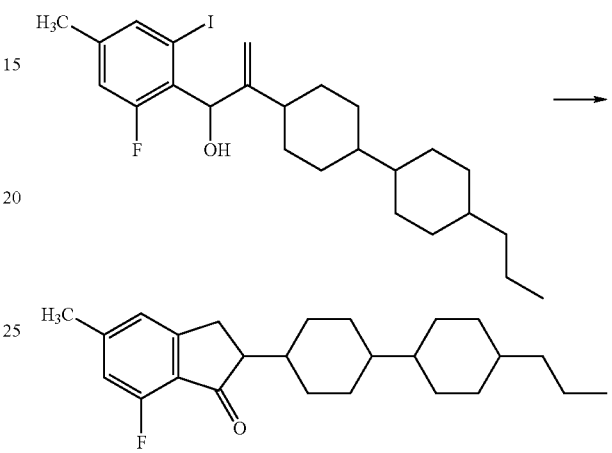

75 g (0.15 mol) of 1-(2-fluoro-6-iodo-4-methylphenyl)-2-(4'-propyl-bicyclohexyl-4-yl)-prop-2-en-1-ol, 50 ml of triethylamine, 400 mg of palladium(II) acetate (1.8 mmol) and 960 mg (3.7 mmol) of triphenylphosphine are dissolved in 200 ml of acetonitrile and refluxed overnight. The mixture is cooled down to room temperature and subjected to conventional workup.

Yield 44.5 g (80% of theory)

Example 3

14-Propyl-4'-(1,1,7-trifluoro-5-methylindan-2-yl)bicyclohexyl

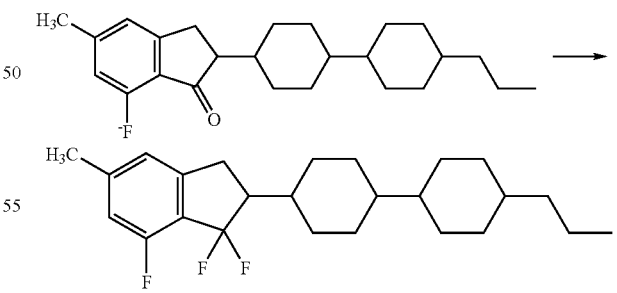

44.5 g (0.12 mol) of 7-fluoro-5-methyl-2-(4'-propylbicyclohexyl-4-yl)indan-1-one are dissolved in 400 ml of dichloromethane and the solution is treated with 32.4 g (0.3 mol) of $SF_4$ in an autoclave at room temperature. After the reaction has ended, the mixture is subjected to conventional work-up.

Yield 33.5 g (71% of theory)

Example 4

4'-(3,4-Difluoro-6-methyl-1H-inden-2-yl)4-propylbicyclohexyl

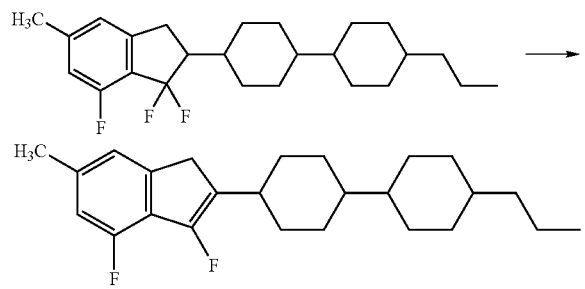

10.0 g (0.025 mol) of 4-propyl-4'-(1,1,7-trifluoro-5-methylindan-2-yl)-bicyclohexyl are stirred together with 5.6 g of potassium tert-butylate in 200 ml of tetrahydrofuran at 60° C. for 6 hours. The mixture is then subjected to conventional work-up.

Yield 5.9 g (63% of theory)

Example 5

4'-(4-Fluoro-6-methyl-3-trifluoromethyl-1H-inden-2-yl)4-propylbicyclohexyl

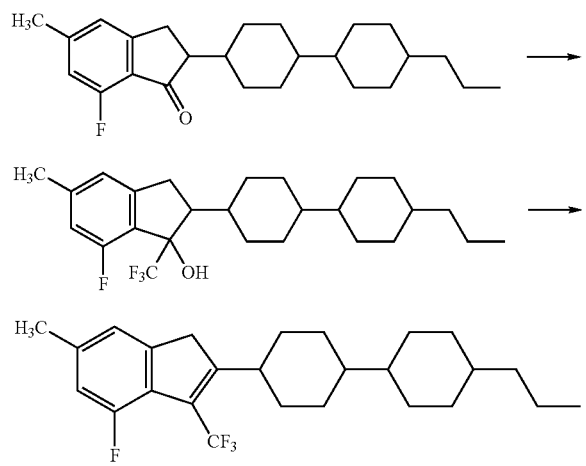

8.5 g (0.023 mol) of 7-fluoro-5-methyl-2-(4'-propylbicyclohexyl-4-yl)-indan-1-one are dissolved in 50 ml of tetrahydrofuran and the solution is cooled down to 0° C. 3.7 ml (0.025 mol) of trifluoromethyltrimethylsilane are added. 0.1 ml of tetrabutylammonium fluoride (1 M solution in THF) are added. After the reaction has ended, the mixture is subjected to conventional workup, and then the product is taken up in 40 ml of methanol, 200 mg of potassium fluoride are added and the mixture is refluxed for 10 hours. The resulting carbinol is dissolved in 30 ml of pyridine and 1.7 ml (0.024 mol) of thionyl chloride are added dropwise. The mixture is stirred for 10 hours at room temperature and then subjected to conventional workup.

Yield 6.9 g (71% of theory)

Example 6

2-Iodo-4-methyl-6-fluorophenol

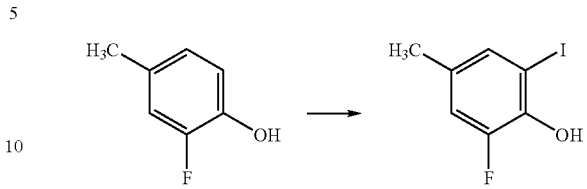

55.5 g (0.44 mol) of 2-fluoro-4-methylphenol and 120.3 g (0.87 mol) of potassium carbonate are dissolved in 275 ml of water and the solution is cooled down to 5° C. 127.5 g of iodine (0.5 mol) are added in portions.

After the reaction has ended, the mixture is subjected to conventional work-up.

Yield 86.5 g (78% of theory)

Example 7

7-Fluoro-5-methyl-2-(4'-propylbicyclohexyl-4-yl)-benzofuran

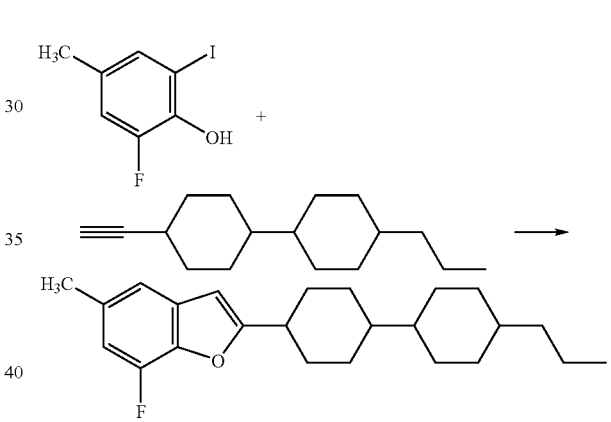

46.5 g (0.2 mol) of 4'-propylbicyclohexylacetylene, dissolved in dimethyl-formamide, are added dropwise to an initial charge of 50.5 g (0.2 mol) of 2-iodo-4-methyl-6-fluorophenol, 4.2 g (6 mmol) of bis(triphenylphosphine)-palladium(II) chloride, 1.2 g (6.3 mmol) of copper(I) iodide and 40.5 g (0.4 mol) of triethylamine in 200 ml of dimethylformamide at room temperature. The mixture is stirred for one hour at room temperature and for 2 hours at 40° C. and then subjected to conventional workup.

Yield 38.5 g (54% of theory)

The compound can be converted into the dihydrobenzofuran by hydro-genation under atmospheric pressure using palladium-on-carbon (10%).

Example 8

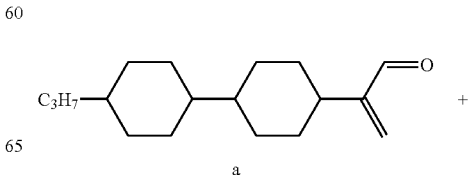

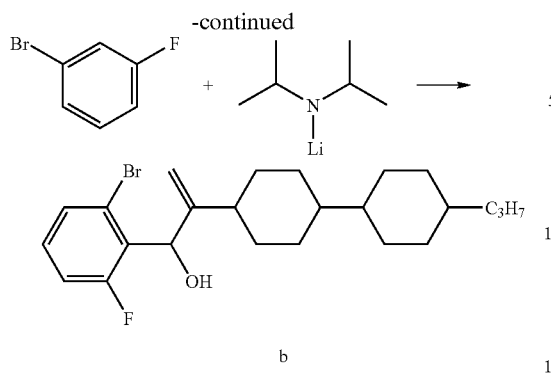

b

An initial charge of 41.0 ml of a 2 molar solution of lithium diisopropylamide in cyclohexane/ethylbenzene/tetrahydrofuran (79.612 mmol) and 150 ml of THF is treated with 60.3 g (93.143 mmol) of 1-bromo-3-fluorobenzene in 20 ml of THF at −74° C. The mixture is stirred for 1 hour followed by addition of a solution of 18.4 g (70.111 mmol) of a in 40 ml of THF. The mixture is stirred for 12 hours, acidified with 1 n HCL and extracted with methyl t-butyl ether. The organic phase is dried and evaporated and the product is crystallized from n-hexane.

Yield 25.9 g (84.4% of theory)

Example 9

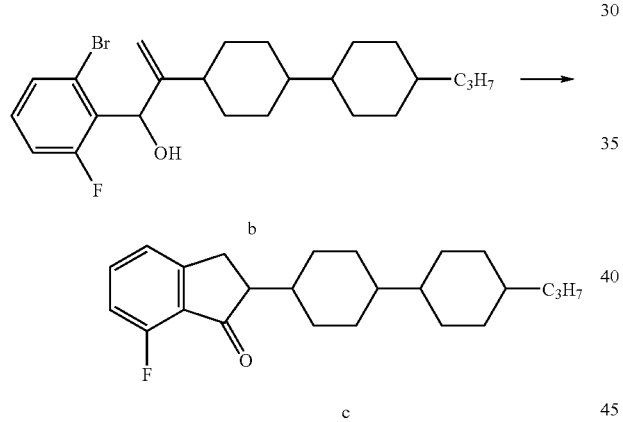

95.8 g (58.98 mmol) of b are dissolved in a warm mixture of 185 ml of acetonitrile and 40 ml of triethylamine. 2.5 g (2.538 mmol) of bis-(tri-o-tolylphosphine)palladium(II) chloride catalyst are added to this solution. The mixture is heated to 90° C. under nitrogen and then subjected to conventional work-up. Crystallization from hexane yields 16.2 g of c.

Yield 16.2 g (77.0% of theory)

Example 10

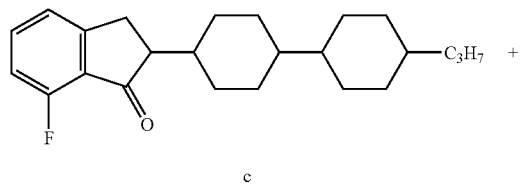

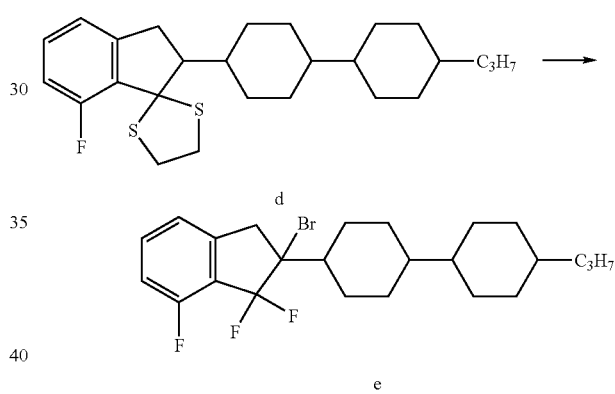

d 5.9 g (16.548 mmol) of c and 3.207 ml (32.0 mmol) of 1,3-propanedithiol are dissolved in 50 ml of dichloromethane. 10 ml (79.617 mmol) of boron trifluoride diethylether complex are added to this solution at −10° C. The mixture is stirred at −5 to −10° C. and then allowed to warm to room temperature overnight. The product solution is poured over bicarbonate and the mixture is stirred until gas evolution has ceased. The mixture is extracted twice with dichloromethane, dried and chromatographed using a methyl t-butyl ether/heptane mixture (1:10).

Example 11

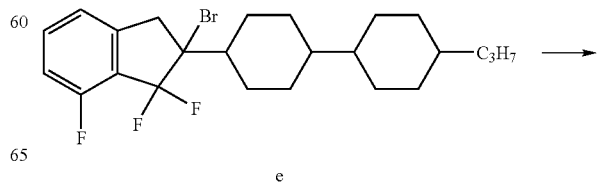

An initial charge of 41 ml of a 65% strength hydrogen fluoride solution in pyridine and 11.4 g (39.87 mmol) of 1,3-dibromo-5,5-dimethylhydantoin in 35 ml of dichloromethane is cooled down to −75° C. 4.1 g (9.178 mmol) of d in 25 ml of dichloromethane are added to this solution. The cooling bath is removed and the reaction mixture is stirred overnight. 200 ml of ice-cooled sodium bisulfite solution and 500 ml of 2 n NaOH are added. The aqueous phase is extracted three times with dichloromethane and the organic phase is washed with saturated sodium chloride solution, dried and evaporated. The product is chromatographed using diethyl ether/heptane (1:20).

Example 12

-continued

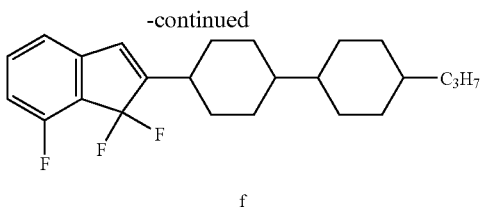

f 8 ml of diazabicyclo[5.4.0]undec-7-ene in 8 ml of THF are added to 4.20 g of the raw product from Example 12. The mixture is stirred at room temperature until the reaction is complete (TLC). The mixture is then evaporated, the residue is taken up in water and dichloromethane, extracted, dried and chromatographed using hexane.

Example 13

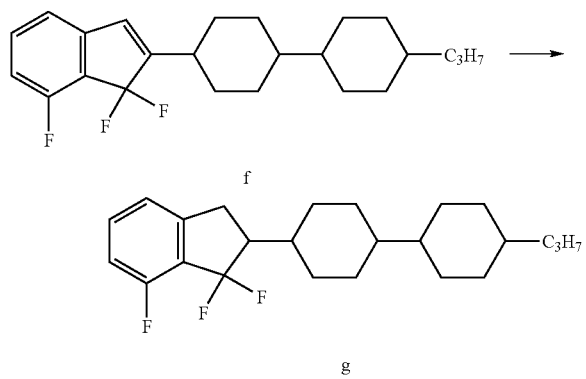

2.3 g of the raw product from Example 12 are hydrogenated over 1.8 g of 5% palladium on carbon in 30 ml of tetrahydrofuran.

The following compounds are obtained in analogy to Examples 8–13:

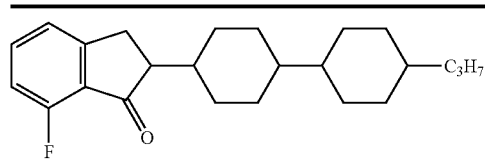

Phases: K 122 I
Cl.p.: 23.7° C.
Δε: −8.5
Δn: 0.075

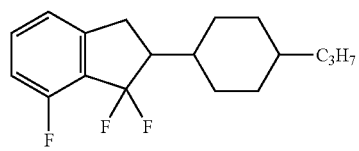

Phases: K 99 I
Cl.p.: 18.1° C.
Δε: −7.1
Δn: 0.086

-continued

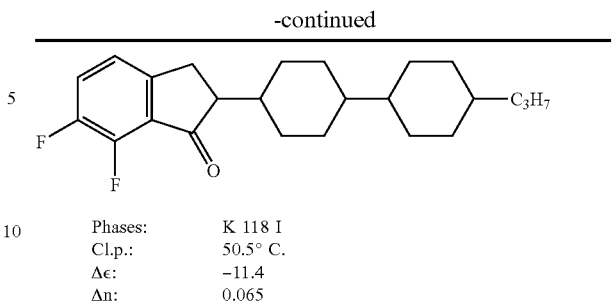

Phases: K 118 I
Cl.p.: 50.5° C.
Δε: −11.4
Δn: 0.065

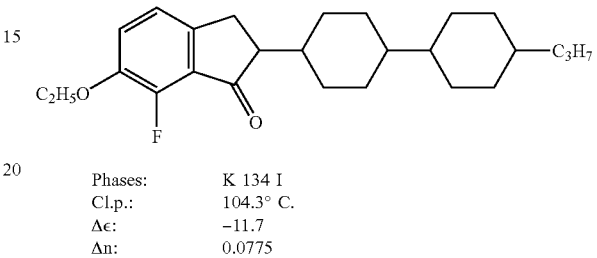

Phases: K 134 I
Cl.p.: 104.3° C.
Δε: −11.7
Δn: 0.0775

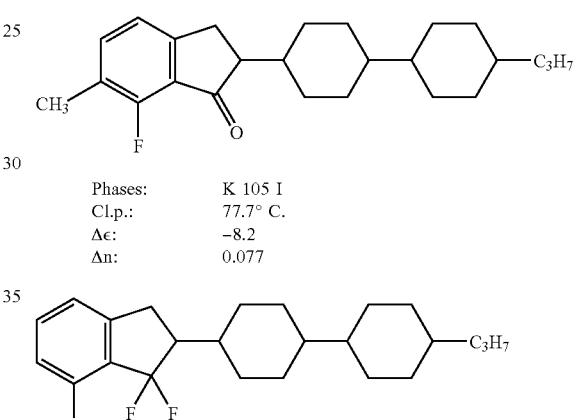

Phases: K 105 I
Cl.p.: 77.7° C.
Δε: −8.2
Δn: 0.077

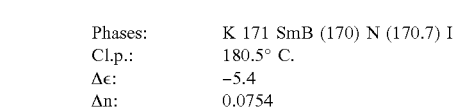

Phases: K 171 SmB (170) N (170.7) I
Cl.p.: 180.5° C.
Δε: −5.4
Δn: 0.0754

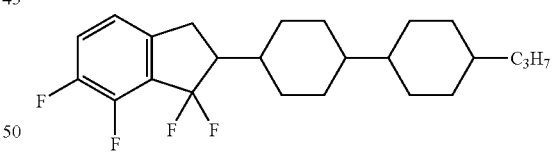

Phases: K 130 SmB 168 N 203.7 I
Cl.p.: 202.3° C.
Δε: −8.3
Δn: 0.075

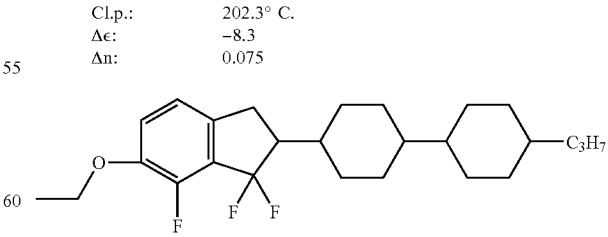

Phases: K 109 SmA-1 156 SmA-2 183 N 220.7 I
Cl.p.: 253.5° C.
Δε: −6.7
Δn: 0.087

-continued

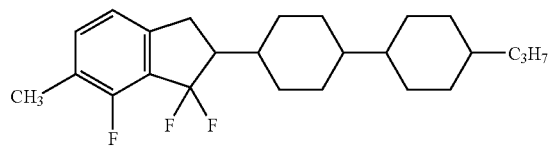

| Phases: | K 110 SmA-1 168 SmA-2 171 N 207.0 I |
| --- | --- |
| Cl.p.: | 233.3° C. |
| Δε: | −5.6 |
| Δn: | 0.0765 |

Hereinbefore, cl.p. denotes the clearing point, Δn denotes the dielectric anisotropy and Δn denotes the birefringence.

Mixture Examples

The following abbreviations are used:

CY-n-(O)m

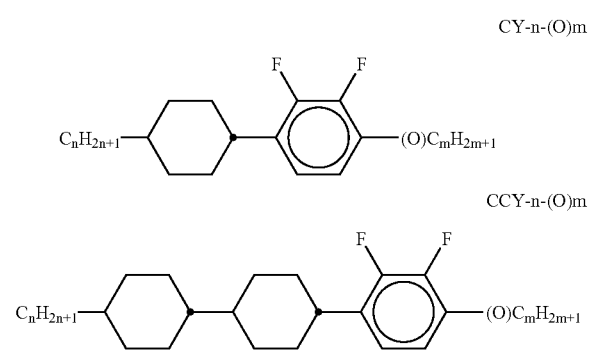

CCY-n-(O)m

CPY-n-(O)m

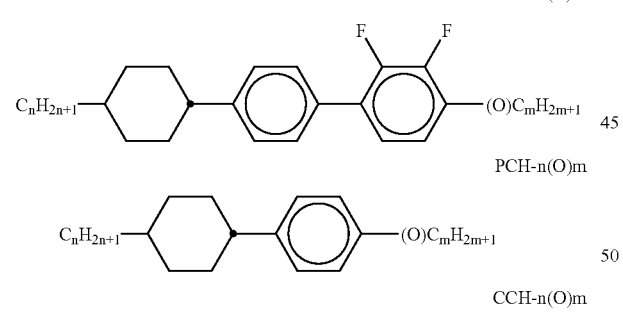

PCH-n(O)m

CCH-n(O)m

CC-nV-m

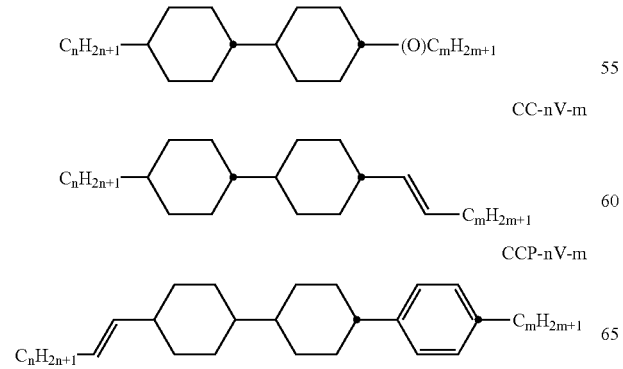

CCP-nV-m

-continued

IND

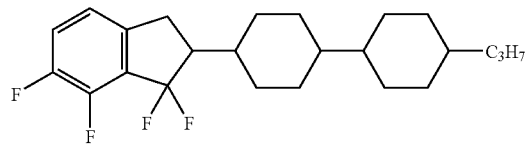

Furthermore:

cl.p. denotes the clearing point [° C.]

Δn denotes the optical anisotropy (birefringence) at 20° C. and 589 nm

Δε denotes the dielectric anisotropy at 20° C. and 1 kHz $\epsilon_\parallel$ denotes the dielectric constant parallel to the director at 20° C. and 1 kHz $K_3/K_1$ denotes the ratio of the elastic constants $K_3$ and $K_1$ $\gamma_1$ denotes the rotational viscosity [mPa·s] (at 20 C. unless stated otherwise)

$V_0$ denotes the capacitive threshold voltage [V]

The capacitive threshold voltage is measured using a display having two plane-parallel outer plates at a separation of 20 μm and electrode layers covered by rubbed polyimide alignment layers on the insides of the outer plates which produce a homeotropic edge alignment of the liquid crystal molecules.

The polymerizable compounds are polymerized in the display by UV irradiation at 28 mW/cm² and for about 2 minutes, simultaneously applying a voltage of 10 V across the display.

The following liquid-crystal mixtures were prepared and used to determine the values below.

Example 14

| CY-3-O2 | 20.00% | Cl.p. | +74.0 |
| --- | --- | --- | --- |
| CY-5-O2 | 11.00% | Δn | 0.0813 |
| CCY-3-O3 | 10.00% | Δε | −3.9 |
| CCY-4-O2 | 10.00% | $\epsilon_\parallel$ | 3.7 |
| CPY-2-O2 | 7.00% | $K_3/K_1$ | 1.04 |
| CC-5-V | 20.00% | $\gamma_1$ | 109 |
| CC-3-V1 | 12.00% | $V_0$ | 2.02 |
| CCH-35 | 5.00% | | |
| IND | 5.00% | | |

Example 15

| CY-3-O2 | 12.00% | Cl.p. | +75.0 |
| --- | --- | --- | --- |
| CY-5-O2 | 12.00% | Δn | 0.0823 |
| CCY-4-O2 | 7.00% | Δε | −3.2 |
| CPY-2-O2 | 12.00% | $\epsilon_\parallel$ | 3.5 |
| CPY-3-O2 | 3.00% | $K_3/K_1$ | 0.97 |
| CC-5-V | 20.00% | $\gamma_1$ | 91 |
| CC-3-V1 | 12.00% | $V_0$ | 2.17 |
| CC-4-V | 10.00% | | |
| CCH-35 | 4.00% | | |
| IND | 8.00% | | |

What is claimed is:

1. A compound having negative Δε of the formula (Ia) or (Ib)

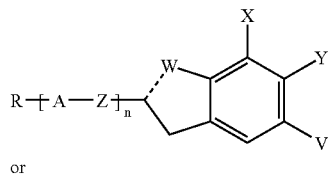

or

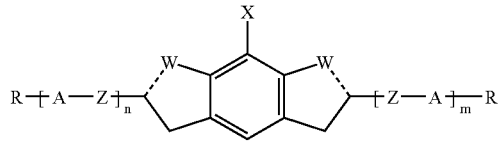

wherein:
- R, in each case independently of one another, is an alkyl or alkoxy radical having 1–12 carbon atoms which is unsubstituted, monosubstituted by —CF₃ or at least monosubstituted by halogen, an oxaalkyl, alkenyl or alkenyloxy radical having 2–12 carbon atoms or an oxaalkenyl radical having 3–12 carbon atoms, where one or more CH₂ groups in these radicals may also, in each case independently of one another, be replaced by —O—, —S—, —CO—, —COO—, —OCO— or —OCO—O— in such a way that heteroatoms are not linked directly to one another,
- A, in each case independently of one another, is 1,4-phenylene, in which =CH— may be replaced once or twice by =N— and which may be mono- to tetrasubstituted, independently of one another, by halogen, —CN, —CH₃, —CH₂F, —CHF₂, —CF₃, —OCH₃, —OCH₂F, —OCHF₂ or —OCF₃, 1,4-cyclohexylene, 1,4-cyclohexenylene or 1,4-cyclohexadienylene, in which —CH₂— may be replaced once or twice by, independently of one another, —O— or —S— and which may be mono- or polysubstituted by halogen,
- Z, in each case independently of one another, is a single bond, a —CH₂—CH₂—, —CF₂CF₂—, —CH=CH—, —CF=CH—, —CH=CF—, —C≡C—, —CO—O—, —O—CO—, —O—CH₂—, —CH₂—O—, O—CF₂— or a —CF₂—O— group,
- X is —F, —Cl, —CN, —NCS, —CF₃, —OCF₃, or —OCHF₂,
- Y, V each is, independently of one another, hydrogen, or alkyl having 1–15 carbon atoms, alkoxy having 2–15 carbon atoms, alkenyl having 2–15 carbon atoms, or alkynyl having 1–15 carbon atoms, which is unsubstituted, monosubstituted by —CF₃ or at least monosubstituted by halogen where one or more CH₂ groups in these radicals may also, in each case independently of one another, be replaced by —O—, —S—, —CO—, —COO—, —OCO— or —OCO—O— in such a way that heteroatoms are not linked directly to one another,
- Y is additionally —F or —Cl,
- W, in each case independently of one another, is —O—, —C(O)—, —CHF— or —CF₂— or —CH= or —CF= and, in formula (Ib), additionally —CH₂—
- n, m each is, independently of one another, 0, 1, 2, 3 or 4 and the dotted line is a single bond or a double bond, with the proviso that n in formula (Ia) is 1, 2, 3, or 4.

2. A compound according to claim 1, which is:

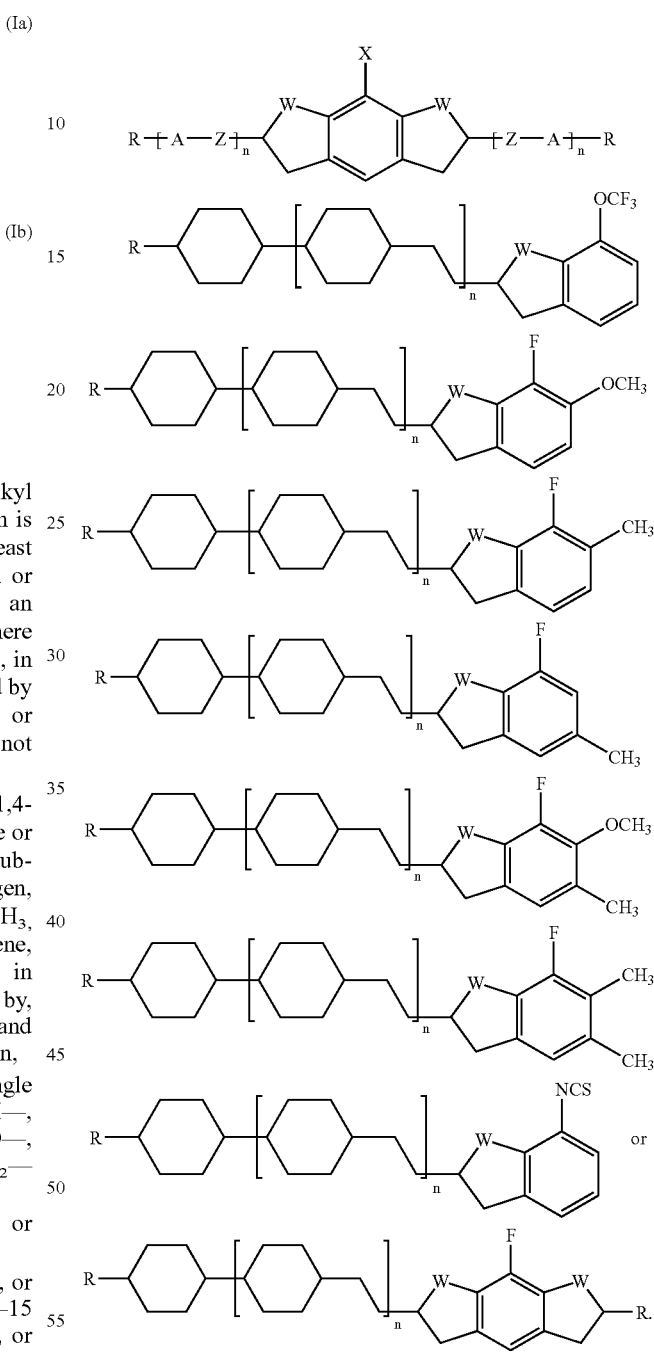

3. A compound according to claim 1, which is:

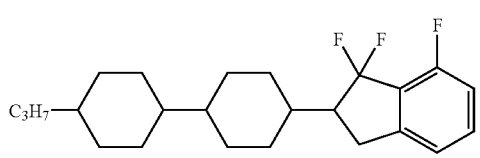

-continued

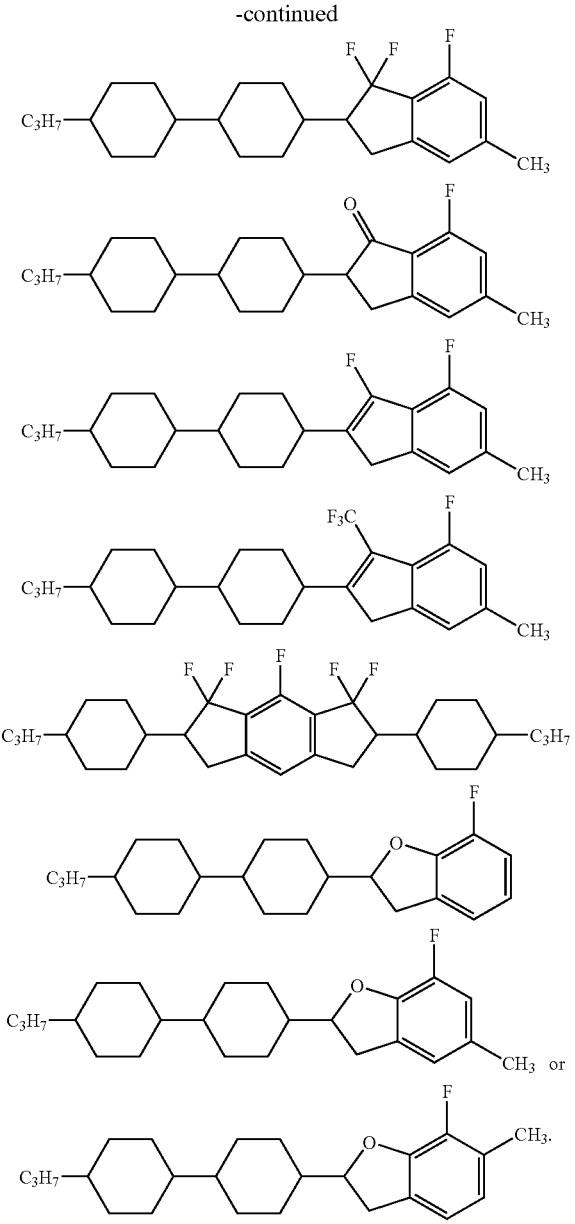

4. A liquid-crystalline medium comprising at least two liquid-crystalline compounds including at least one compound of the formulae (Ia) and/or (Ib)

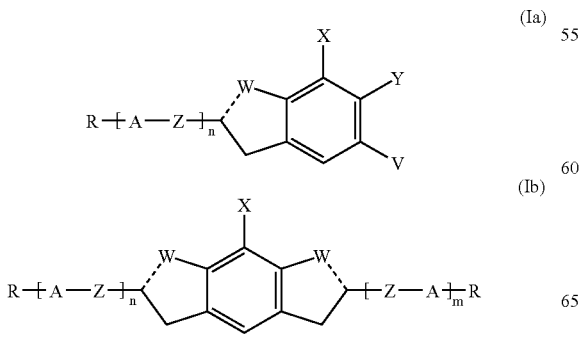

wherein:

R, in each case independently of one another, is an alkyl or alkoxy radical having 1–12 carbon atoms which is unsubstituted, monosubstituted by —$CF_3$ or at least monosubstituted by halogen, an oxaalkyl, alkenyl or alkenyloxy radical having 2–12 carbon atoms or an oxaalkenyl radical having 3–12 carbon atoms, where one or more $CH_2$ groups in these radicals may also, in each case independently of one another, be replaced by —O—, —S—, —CO—, —COO—, —OCO— or —OCO— in such a way that heteroatoms are not linked directly to one another, A, in each case independently of one another, is 1,4-phenylene, in which =CH— may be replaced once or twice by =N— and which may be mono- to tetrasubstituted, independently of one another, by halogen, —CN, —$CH_3$, —$CH_2F$, —$CHF_2$, —$CF_3$, —$OCH_3$, —$OCH_2F$, —$OCHF_2$ or —$OCF_3$, 1,4-cyclohexylene, cyclohexylene, 1,4-cyclohexenylene or 1,4-cyclohexadienylene, in which —$CH_2$— may be replaced once or twice by, independently of one another, —O— or —S— and which may be mono- or polysubstituted by halogen, Z, in each case independently of one another, is a single bond, a —$CH_2$—$CH_2$—$CH_2$—, —$CF_2CF_2$—, —CH=CH—, —CF=CH—, —CH=CF—, —C≡C—, —CO—O—, —O—CO—, —O—$CH_2$—, —$CH_2$—O—, O—$CF_2$— or a —$CF_2$—O— group, X is —F, —Cl, —CN, —NCS, —$CF_3$, —$OCF_3$, or —$OCHF_2$, Y, V each is, independently of one another, hydrogen, or alkyl having 1–15 carbon atoms, alkoxy having 1–15 carbon atoms, alkenyl having 2–15 carbon atoms, or alkynyl having 2–15 carbon atoms, which is unsubstituted monosubstituted by —$CF_3$ or at least monosubstituted by halogen where one or more $CH_2$ groups in these radicals may also, in each case independently of one another, be replaced by —O—, —S—, —CO—, —COO—, —OCO— or —OCO—O— in such a way that heteroatoms are not linked directly to one another, Y is additionally —F or —Cl, W, in each case independently of one another, is —O—, —C(O)—, —CHF— or —$CF_2$— or —CH= or —CF= and, in formula (Ib), additionally —$CH_2$— n,m each is, independently of one another, 0, 1, 2, 3 or 4 and the dotted line is a single bond or a double bond.

5. An electro-optical liquid-crystal display comprising a liquid-crystalline medium according to claim 4.

6. A compound according to claim 1 of formula (Ia) or (Ib),

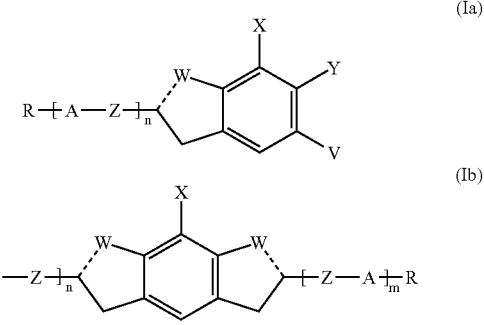

wherein:
- R, in each case independently of one another, is an alkyl or alkoxy radical having 1–12 carbon atoms which is unsubstituted, monosubstituted by —$CF_3$ or at least monosubstituted by halogen, an oxaalkyl, oxaalkenyl or alkenyloxy radical having 2–12 carbon atoms or an oxaalkenvl radical having 3–12 carbon atoms, where one or more $CH_2$ groups in these radicals may also, in each case independently of one another, be replaced by —O—, —S—, —CO—, —COO—, —OCO— or —OCO—O— in such a way that heteroatoms are not linked directly to one another,
- A, in each case independently of one another, is 1,4-phenylene, in which =CH— may be replaced once or twice by =N— and which may be mono- to tetrasubstituted, independently of one another, by halogen. —CN, —$CH_3$, —$CH_2F$, —$CHF_2$, —$CF_3$, —$OCH_3$, —$OCH_2F$, —$OCHF_2$ or —$OCF_3$ 1,4—cyclohexylene, 4-cyclohexenylene or 1,4-cyclohexadienylene, in which —$CH_2$— may be replaced once or twice by, independently of one another, —O— or —S— and which may be mono- or polysubstituted by halogen,
- Z, in each case independently of one another, is a single bond, a —$CH_2$—$CH_2$—, —$CF_2CF_2$—, —CH=CH—, —CF=CH—, —CH=CF—, —C≡C—, —CO—O—, —O—CO—, —O—$CH_2$—, —$CH_2$—O—, O—$CF_2$— or a —$CF_2$—O— group,
- X is —F, —Cl, —CN, —NCS, —$CF_3$—$OCF_3$, or —$OCHF_2$,
- Y, V each is, independently of one another, hydrogen, or alkyl having 1–15 carbon atoms, alkoxy having 1–15 carbon atoms, alkenyl having 2–15 carbon atoms, or alkynyl having 2–15 carbon atoms, which is unsubstituted, monosubstituted by —$CF_3$ or at least monosubstituted by halogen where one or more $CH_2$ groups in these radicals may also, in each case independently of one another, be replaced by —O—, —S—, —CO—, —COO—, —OCO— or —OCO—O— in such a way that heteroatoms are not linked directly to one another,
- Y is additionally —F or —Cl,
- W, in each case independently of one another, is —O—, —C(O)—, —CHF— or —$CF_2$— or —CH= or —CF= and, in formula (Ib). additionally —$CH_2$—
- n,m each is, independently of one another, 0, 1, 2, 3 or 4 and the dotted line is a single bond or a double bond,
- wherein at least one of Y and V is, independently, an alkyl, alkoxy, alkenyl, or alkynyl radical having 2–15 carbon atoms which is unsubstituted, monosubstituted by —$CF_3$ or at least monosubstituted by halogen where one or more $CH_2$ groups in these radicals may also, in each case independently of one another, be replaced by —O, —S—, —CO—, —COO—, —OCO—, or —OCO—O— in such a way that heteroatoms are not linked to one another.

7. A compound according to claim 6, wherein V is, independently, an alkyl, alkoxy, alkenyl or alkynyl radical having 2–15 carbon atoms which is unsubstituted, monosubstituted by —$CF_3$ or at least monosubstituted by halogen where one or more $CH_2$ groups in these radicals may also, in each case independently of one another, be replaced by —O, —S—, —CO—, —COO—, —OCO—, or —OCO—O— in such a way that heteroatoms are not linked to one another.

8. A compound according to claim 1, wherein X is F.

9. A compound according to claim 1, wherein A is, independently, unsubstituted or substituted 1,4-phenylene, unsubstituted or substituted 1,4—cyclohexylene wherein —$CH_2$— is optionally replaced once or twice by —O—, or unsubstituted or substituted 1,4—cyclohexenylene.

10. A compound according to claim 1, wherein at least one of R, Y and V is, independently, methyl, ethyl, propyl, butyl, pentyl, hexyl, methoxy, ethoxy, propoxy, butoxy, pentoxy, hexoxy, or heptoxy.

11. A compound according to claim 1, wherein at least one of R, Y, and V is, independently, a straight-chain or branched alkenyl radical having 2–15 carbon atoms.

12. A compound according to claim 1, wherein at least one of R, Y, and V is, independently, an alkyl radical having 1–15 carbon atoms wherein one $CH_2$ group has been replaced by —O—and one has been replaced by —CO—.

13. A compound according to claim 1, wherein at least one of R, Y and V is, independently, an alkyl radical having 1–15 carbon atoms in which one $CH_2$ group has been replaced by unsubstituted or substituted —CH=CH— and an adjacent $CH_2$ group has been replaced by —CO—, —CO—O— or —O—CO—.

14. A compound according to claim 1, wherein at least one of R, Y and V is, independently, an alkyl radical having 1–15 carbon atoms or an alkenyl radical having 2–15 carbon atoms which is monosubstituted by —CH or —$CF_3$.

15. A compound according to claim 1, wherein at least one of R, Y and V is, independently, an alkyl radical having 1–15 carbon atoms or an alkenyl radical having 2–15 carbon atoms which is at least monosubstituted by halogen.

16. A compound according to claim 1, wherein at least one of R, Y and V is, independently, an alkyl radical wherein two or more $CH_2$ groups are replaced by —O— and/or —CO—O—.

17. A compound according to claim 1, wherein at least one of R, Y and V is, independently, hydrogen or an alkyl, alkoxy or alkenyl radical having 1–7 carbon atoms.

18. A compound according to claim 1, having a negative Δε of —11.7 to —5.4.

19. A compound according to claim 1, wherein said compound is of one of the following formulas:

The following structures are very particularly preferred:

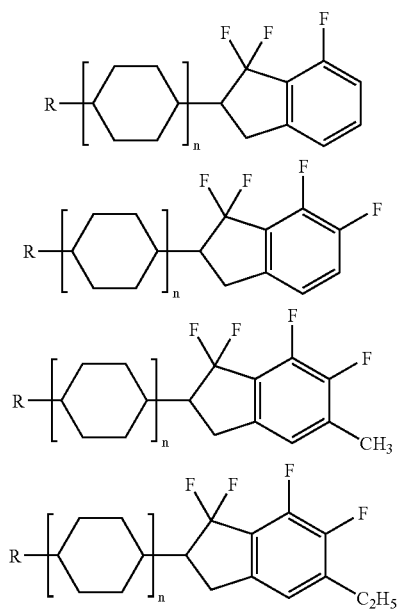

-continued

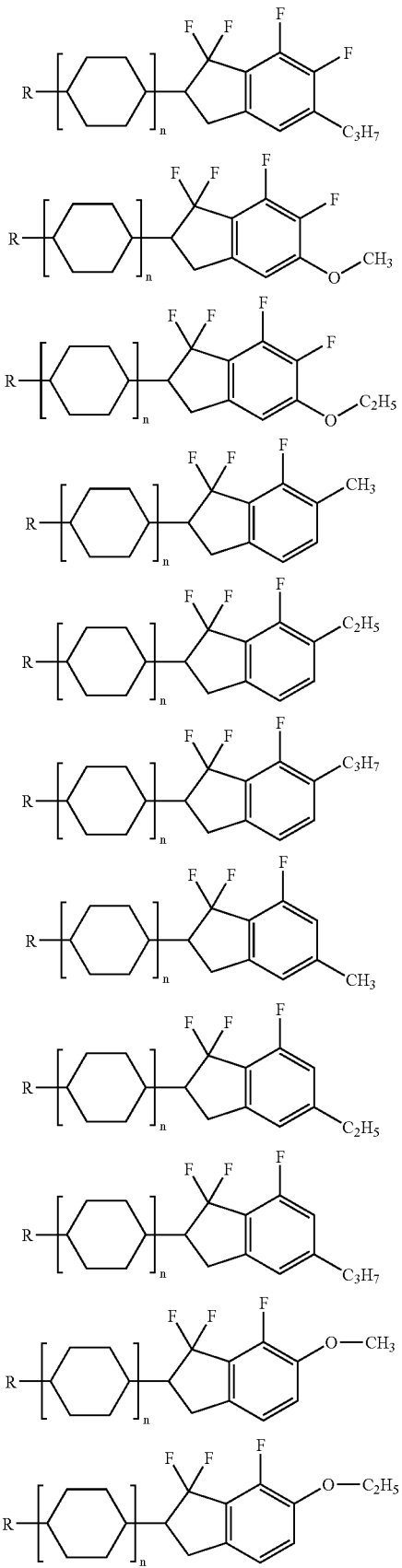

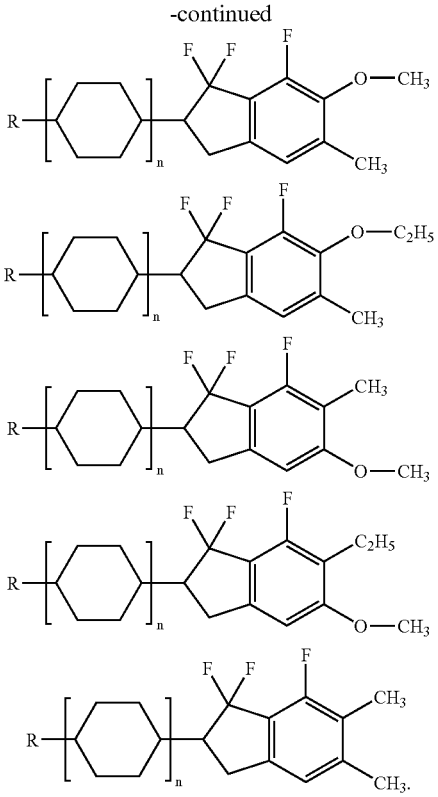

20. A compound according to claim 19, wherein n is 1 and R is n-alkyl having 1 to 12 carbon atoms.

21. A compound according to claim 20, wherein R is $C_1$–$C_5$-alkyl.

22. A compound according to claim 19, wherein n is 2 and R is n-alkyl having 1 to 12 carbon atoms.

23. A compound according to claim 22, wherein R is $C_1$–$C_5$-alkyl.

24. A compound according to claim 19, wherein n is 1 and R is n-alkenyl having 2 to 12 carbon atoms.

25. A compound according to claim 24, wherein R is vinyl, prop-1-enyl, but -1-enyl or but-3-enyl.

26. A compound according to claim 19, wherein n is 2 and R is n-alkenyl having 2 to 12 carbon atoms.

27. A compound according to claim 26, wherein R is vinyl, prop-1-enyl, but -1-enyl or but-3-enyl.

28. A compound according to claim 1, wherein A is in each case, independently of one another,

-continued

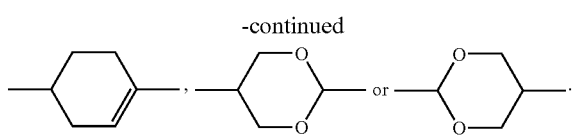

29. A compound according to claim 1, wherein at least one of R, Y and V is methyl, ethyl, propyl, butyl, pentyl, hexyl, heptyl, methoxy, ethoxy, propoxy, butoxy, pentoxy hexoxy, heptoxy, 2-oxapropyl, 2-oxabutyl, 3-oxabutyl, 2-, 3- or 4-oxapentyl, 2-, 3-, 4- or 5-oxahexyl, 2-, 3-, 4-, 5- or 6-oxaheptyl, vinyl, prop-i- or prop-2-enyl, but-1-, -2- or but-3-enyl, pent-1-, -2-, -3- or pent-4-enyl, hex-1-, -2-, -3-, -4- or hex-5-enyl, or hept-1-, -2-, -3-, -4-, -5- or -6-enyl.

30. A compound according to claim 1, wherein Z is a single bond, —CH$_2$—CH$_2$——CH$_2$—O—, or —O—CH$_2$—.

* * * * *

UNITED STATES PATENT AND TRADEMARK OFFICE
CERTIFICATE OF CORRECTION

| | | |
|---|---|---|
| PATENT NO. | : 7,122,228 B2 | |
| APPLICATION NO. | : 10/484193 | |
| DATED | : October 17, 2006 | |
| INVENTOR(S) | : Matthias Bremer | |

It is certified that error appears in the above-identified patent and that said Letters Patent is hereby corrected as shown below:

Column 45, line 49, reads "O-CF$_2$-" should read -- -O-CF$_2$- --
Column 45, line 57, reads "alkynyl having 1-15 carbon atoms," should read -- alkynyl having 2-15 carbon atoms. --
Column 45, line 67, reads "-CH$_2$-" should read -- -CH$_2$-, --
Column 46, line 3, reads "1. 2. 3, or 4." should read -- 1, 2, 3, or 4. --
Column 48, line 12, reads "-OCO-" should read -- -OCO-O- --
Column 48, line 19, reads "-OCH$_2$," should read -- -OCH$_3$, --
Column 48, line 19-20, reads "1,4-cyclohexylene, cyclohexylene, 1,4-cyclohexenylene" should read -- 1,4-cyclohexylene, 1,4-cyclohexenylene --
Column 48, line 27, reads "-CH$_2$-CH$_2$-CH$_2$-," should read -- -CH$_2$-CH$_2$, --
Column 48, line 30, reads "O-CF$_2$-" should read -- -O-CF$_2$- --
Column 48, line 36-37, reads "unsubstituted monosubstituted" should read -- unsubstituted, monosubstituted --
Column 48, line 46, reads "-CH$_2$-n.m" should read -- -CH$_2$- (start new line) n, m --
Column 49, line 5, reads "oxaalkenyl" should read -- alkenyl --
Column 49, line 7, reads "oxaalkenvl" should read -- oxaalkenyl --
Column 49, line 18, reads "-OCF$_3$1,4-" should read -- -OCF$_3$, 1,4- --
Column 49, line 19, reads "4-cyclohexenylene" should read -- 1,4-cyclohexenylene --
Column 49, line 29, reads "-CF$_3$-OCF$_3$," should read -- -CF$_3$-, -OCF$_3$, --
Column 49, line 44, reads "-CH$_2$-" should read -- -CH$_2$-, --
Column 49, line 53, reads "-O," should read -- -O-, --
Column 49, line 62, reads "-O," should read -- -O-, --
Column 50, line 14, reads "-O-and" should read -- -O- and --
Column 50, line 41, delete "The... preferred."
Column 53, line 11, reads "pentoxy hexoxy," should read -- pentoxy, hexoxy, --
Column 54, line 3, reads "prop-i" should read -- prop-1 --
Column 54, line 4, reads "but-3-enyl," should read -- -3-enyl, --
Column 54, line 4, reads "pent-4-enyl," should read -- -4-enyl, --

Signed and Sealed this
Sixteenth Day of August, 2011

David J. Kappos
*Director of the United States Patent and Trademark Office*

CERTIFICATE OF CORRECTION (continued)
U.S. Pat. No. 7,122,228 B2

Column 54, line 5, reads "hex 5-enyl," should read -- -5-enyl, --
Column 54, line 7, reads "-$CH_2$-$CH_2$-$CH_2$-O-," should read -- -$CH_2$-$CH_2$-, -$CH_2$-O-, --